(12) United States Patent
Hamrick et al.

(10) Patent No.: US 11,858,908 B2
(45) Date of Patent: Jan. 2, 2024

(54) COMPOSITIONS AND METHODS FOR INHIBITING IDO1

(71) Applicant: Augusta University Research Institute, Inc., Augusta, GA (US)

(72) Inventors: Mark Hamrick, Evans, GA (US); Carlos Isales, Augusta, GA (US); Iryna Lebedyeva, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 17/579,505

(22) Filed: Jan. 19, 2022

(65) Prior Publication Data

US 2022/0227727 A1 Jul. 21, 2022

Related U.S. Application Data

(60) Provisional application No. 63/139,079, filed on Jan. 19, 2021.

(51) Int. Cl.
| | |
|---|---|
| *C07C 69/66* | (2006.01) |
| *C07D 317/60* | (2006.01) |
| *C07D 311/06* | (2006.01) |
| *C07D 405/12* | (2006.01) |

(52) U.S. Cl.
CPC ............ *C07D 317/60* (2013.01); *C07C 69/66* (2013.01); *C07D 311/06* (2013.01); *C07D 405/12* (2013.01)

(58) Field of Classification Search
CPC .................................................. C07C 69/66
See application file for complete search history.

(56) References Cited

U.S. PATENT DOCUMENTS

| | | | | |
|---|---|---|---|---|
| 4,329,361 | A | * | 5/1982 | Zenk .................... A61K 31/215 514/533 |
| 5,948,433 | A | | 9/1999 | Burton |
| 5,985,311 | A | | 11/1999 | Cordes |
| 6,461,644 | B1 | | 10/2002 | Jackson |
| 6,676,961 | B1 | | 1/2004 | Lichter |

OTHER PUBLICATIONS

Chan, "Frailty in Older People", The Hong Kong Medical Diary, 13(9):7-9 (2008).
Cruz-Jentoft, et al., "Sarcopenia: European consensus on definition and diagnosis: Report of the European Working Group on Sarcopenia in Older People", Age and Aging, 39(4):412-423 (2010).
Espinoza and Walston, "Frailty in older adults: insights and interventions", Cleveland Clinic Journal of Medicine, 72(12):1105-1112 (2005).
Fox, et al., "Transdermal Drug Delivery Enhancement by Compounds of Natural Origin", Molecules, 16:10507-10540 (2011).
Fried, et al., "Frailty in Older Adults: Evidence for a Phenotype", Journal of Gerontology: Medical Sciences, 56A(3):M146-156 (2001).
Kaiser, et al., "Kynurenine, a Tryptophan Metabolite That Increases with Age, Induces Muscle Atrophy and Lipid Peroxidation", Oxid. Med. Cell. Longev., 2019:9894238 (2019).
Lang, et al., "Sarcopenia: etiology, clinical consequences, intervention, and assessment", Osteoporosis Int, 21(4):543-559 (2010).
Meng, et al., "Molecular docking: a powerful approach for structure-based drug discovery", Curr. Comput. Aided Drug Des., 7(2):146-157 (2011).
Pathan and Setty, "Chemical Penetration Enhancers for Transdermal Drug Delivery Systems", Tropical Journal of Pharmaceutical Research, 8(2):173-179 (2009).

* cited by examiner

*Primary Examiner* — Rebecca L Anderson
(74) *Attorney, Agent, or Firm* — PABST PATENT GROUP LLP

(57) ABSTRACT

Provided herein are compounds that inhibit IDO1 and methods of use thereof. Also provided are pharmaceutical compositions and medicaments that include the compounds described herein as well as methods of treating sarcopenia or age-related muscle loss.

5 Claims, 2 Drawing Sheets

COMPOSITIONS AND METHODS FOR INHIBITING IDO1

CROSS-REFERENCE TO RELATED APPLICATION

This application claims the benefit of and priority to U.S. Ser. No. 63/139,079 filed Jan. 19, 2021, and which is incorporated by referenced herein in its entirety.

STATEMENT REGARDING FEDERALLY SPONSORED RESEARCH

This invention was made with government support under AG 036675 awarded by the National Institutes of Health. The government has certain rights in the invention.

TECHNICAL FIELD OF THE INVENTION

Aspects of the invention are generally directed to small molecule inhibitors of 2,3-dioxygenase 1 (IDO1) and methods of use thereof.

BACKGROUND OF THE INVENTION

Sarcopenia or muscle loss with aging is a significant health concern that contributes directly to disability, falls and bone fractures in the elderly. Sarcopenia is the loss of muscle mass, quality and strength associated with aging. Humans begin to lose muscle mass and function at some point in the third decade of life. This loss of muscle mass typically accelerates around age 75. Sarcopenia develops in both physically active and physically inactive people. As the average human lifespan continues to increase, sarcopenia is becoming a significant health concern. The loss of muscle mass from sarcopenia may lead to poor balance, reduced gait speed and frailty. Individuals suffering from sarcopenia are more susceptible to injury and disability, and may be unable to live independently as a result. The spread of sarcopenia will likely result in increases in health care and assisted living expenses.

The essential amino acid Tryptophan (Trp) is catabolized through the kynurenine (KYN) pathway. The initial rate-limiting step in the kynurenine pathway is performed by heme-containing oxidoreductase enzymes, including tryptophan 2,3-dioxygenase (TDO), indoleamine 2,3-dioxygenase-1 (IDO1), and indoleamine 2,3-dioxygenase-2 (IDO2). It has been recently found that the tryptophan metabolite, kynurenine, contributes to the muscle loss with aging by increasing oxidative stress in the skeletal muscle (Kaiser et al., *Oxid. Med. Cell. Longev.* 2019, 9894238). Kynurenine is generated by the enzyme IDO1. Several small molecules have been screened and compounds have been identified that may block IDO1 in primary human skeletal muscle cells and in vascular smooth muscle cells.

Current experimental treatment regimens for sarcopenia utilize nutritional approaches, exercise training, appetite stimulants and anabolic compounds such as testosterone, but the effects of previously described treatments are not satisfactory. There is a need in the industry for more effective sarcopenia treatments, which desirably result in an increase in muscular mass, strength and force. There is also a need for compounds that are inhibitors of the indoleamine 2,3-dioxygenase-1 and/or indoleamine 2,3-dioxygenase-2 pathway, as well as for methods for treating diseases that can benefit from such inhibition. There has been a considerable amount of effort towards making new IDO1 inhibitors for human use since the discovery of indoleamine, 2,3-dioxygenase 1 as an important target for various therapies. However, only a few potent IDO1 inhibiting compounds have entered clinical trials, and none have been approved by the FDA as of date. Accordingly, there remains a strong unmet need for new IDO1 inhibiting compounds with improved efficacy for sarcopenia treatment and/or prevention.

Therefore, it is an object of the invention to provide IDO1 specific antagonists, for example small molecule IDO1 antagonists.

It is still another object of the invention to provide pharmaceutical compositions containing small molecule IDO1 antagonists that specifically inhibit IDO1.

It is still another embodiment to provide methods of treating muscle wasting or muscle loss.

SUMMARY OF THE INVENTION

IDO1 small molecule inhibitors or antagonists, compositions of the IDO1 small molecule inhibitors or antagonists, and methods of use thereof are provided. In some aspects, the small molecule IDO1 antagonists can lower kynurenine or other downstream tryptophan metabolite levels.

In some aspects, the IDO1 small molecule inhibitors or antagonists can be a compound of Formula Ia:

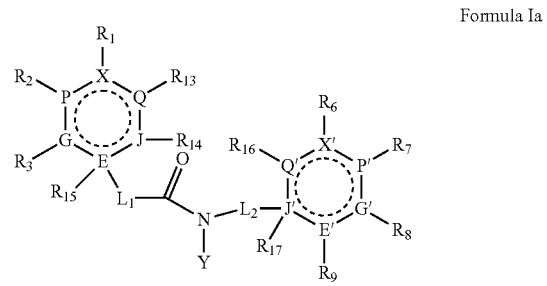

Formula Ia wherein:

X, X', P, P', Q, Q', G, G', J, J', E, and E' are independently C, N, O or S;

$R_1$-$R_3$, $R_6$-$R_9$, and $R_{13}$-$R_{17}$ are independently absent, H, OH, halogen, a substituted or unsubstituted $C_{1\text{-}10}$ alkyl, a substituted or unsubstituted $C_{1\text{-}10}$ alkoxy, a substituted or unsubstituted $C_{3\text{-}10}$ cycloalkyl, a substituted or unsubstituted aryl, or a substituted or unsubstituted heteroaryl, or two neighboring R groups together form a substituted or unsubstituted 3-6 membered carbocycle or substituted or unsubstituted 4-6 membered heterocyclyl containing one or more heteroatom selected from the group consisting of O, S and N;

$L_1$ and $L_2$ are independently a linker, optionally the linker is a substituted or unsubstituted $C_{1\text{-}10}$ alkyl or substituted or unsubstituted $C_{1\text{-}10}$ alkoxy; and Y is H, a substituted or unsubstituted $C_{1\text{-}10}$ alkyl, a substituted or unsubstituted aryl, or a substituted or unsubstituted aralkyl (e.g. a benzyl);

or an enantiomer, tautomer, stereoisomers, solvate, zwitterion, polymorph, prodrug, or a pharmaceutically acceptable salt thereof.

In some aspects of Formula Ia, $L_1$ and $L_2$ are independently

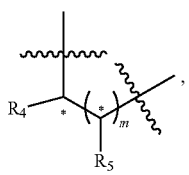

wherein m is an integer from 0 to 10; $R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

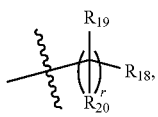

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—COOR$_{10}$, etc.), a hydroxyl, an alkoxy (—OR$_{10}$), a halogen, an amino group (e.g. a primary amino NH$_2$, a secondary amino NHR$_{11}$, or a tertiary amino NR$_{11}$R$_{12}$), an amide group (—CONR$_{11}$R$_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl.

In some aspects, the IDO1 small molecule inhibitor or antagonist contains one or more stereocenters. For example, the stereocenter is one or both of the C* in the linker $L_1$ and $L_2$ having the structure of

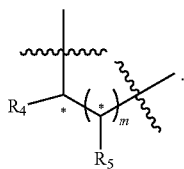

In some aspects, the IDO1 small molecule inhibitors or antagonists can be a compound of Formula Ib:

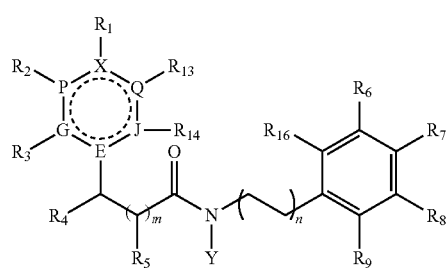

Formula Ib wherein:

X, P, Q, G, J, and E are independently C, N, O or S;

$R_1$-$R_3$, $R_6$-$R_9$, $R_{13}$, $R_{14}$, and $R_{16}$ are independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl, or two neighboring R groups together form a substituted or unsubstituted 3-6 membered carbocycle or substituted or unsubstituted 4-6 membered heterocyclyl containing one or more heteroatom selected from the group consisting of O, S and N;

$R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

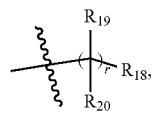

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—COOR$_{10}$, etc.), a hydroxyl, an alkoxy (—OR$_{10}$), a halogen, an amino group (e.g. a primary amino NH$_2$, a secondary amino NHR$_{11}$, or a tertiary amino NR$_{11}$R$_{12}$), an amide group (—CONR$_{11}$R$_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl;

Y is H, a substituted or unsubstituted $C_{1-10}$ alkyl, a substituted or unsubstituted aryl, or a substituted or unsubstituted aralkyl (e.g. a benzyl);

m is an integer from 0 to 10, from 0 to 8, or from 0 to 6, such as 0, 1, 2, 3, 4, 5, 6, 7, 8, 9, or 10; and n is an integer from 1 to 6, such as 1, 2, 3, 4, 5 or 6;

or an enantiomer, tautomer, stereoisomers, solvate, zwitterion, polymorph, prodrug, or a pharmaceutically acceptable salt thereof.

In some forms of Formula Ib, X, P, Q, G, J, and E are independently C or N.

In one aspect, the IDO1 small molecule inhibitors or antagonists can be a compound of Formula Ic:

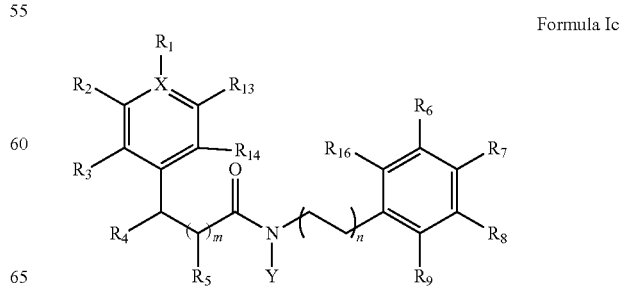

Formula Ic wherein:

X is C, N, O or S;

$R_1$-$R_3$, $R_6$-$R_9$, $R_{13}$, $R_{14}$, and $R_{16}$ are independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl, or two neighboring R groups together form a substituted or unsubstituted 3-6 membered carbocycle or substituted or unsubstituted 4-6 membered heterocyclyl containing one or more heteroatom selected from the group consisting of O, S and N;

$R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

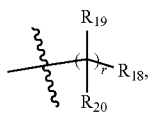

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—COOR$_{10}$, etc.), a hydroxyl, an alkoxy (—OR$_{10}$), a halogen, an amino group (e.g. a primary amino NH$_2$, a secondary amino NHR$_{11}$, or a tertiary amino NR$_{11}$R$_{12}$), an amide group (—CONR$_{11}$R$_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl;

Y is H, a substituted or unsubstituted $C_{1-10}$ alkyl, a substituted or unsubstituted aryl, or a substituted or unsubstituted aralkyl (e.g. a benzyl);

m is an integer from 0 to 10, from 0 to 8, or from 0 to 6, such as 0, 1, 2, 3, 4, 5, 6, 7, 8, 9, or 10; and n is an integer from 1 to 6, such as 1, 2, 3, 4, 5 or 6;

or an enantiomer, tautomer, stereoisomers, solvate, zwitterion, polymorph, prodrug, or a pharmaceutically acceptable salt thereof.

In some aspects of Formula Ib and/or Formula Ic, $R_2$ and $R_3$ together and/or $R_{13}$ and $R_{14}$ together form a substituted or unsubstituted 3-6 membered carbocycle or substituted or unsubstituted 4-6 membered heterocyclyl containing one or more heteroatom selected from the group consisting of O, S and N, and/or $R_{16}$ and $R_6$ together, $R_6$ and $R_7$ together, $R_7$ and $R_8$ together, and/or $R_8$ and $R_9$ together, form a substituted or unsubstituted 3-6 membered carbocycle or substituted or unsubstituted 4-6 membered heterocyclyl containing one or more heteroatom selected from the group consisting of O, S and N.

In some aspects of Formula Ib and/or Formula Ic, $R_2$ and $R_3$ together form a substituted or unsubstituted 3-6 membered carbocycle or substituted or unsubstituted 4-6 membered heterocyclyl containing one or more heteroatom selected from the group consisting of O, S and N. In some aspects of Formula Ib and/or Formula Ic, $R_6$ and $R_7$ together or $R_7$ and $R_8$ together form a substituted or unsubstituted 3-6 membered carbocycle or substituted or unsubstituted 4-6 membered heterocyclyl containing one or more heteroatom selected from the group consisting of O, S and N.

In one aspect, the IDO1 small molecule inhibitors or antagonists can be a compound of Formula I:

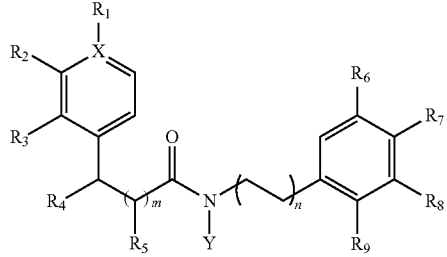

Formula I wherein

X is each independently C, CH or N;

$R_1$ is independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl;

$R_2$ and $R_3$ together form a substituted or unsubstituted 3-6 membered carbocycle or a substituted or unsubstituted 4-6 membered heterocyclyl containing one or more heteroatom selected from the group consisting of O, S and N; or $R_2$ and $R_3$ are each independently H, OH, halogen, a substituted or unsubstituted $C_{1-10}$ alkyl, a substituted or unsubstituted $C_{1-10}$ alkoxy, a substituted or unsubstituted aryl, or a substituted or unsubstituted heteroaryl;

$R_4$ and each occurrence of $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, COOH, —COOR$_{10}$, —CONH$_2$, —NCO, —CHO, —CN, NO$_2$, NH$_2$, NHR$_{11}$, NR$_{11}$R$_{12}$, or

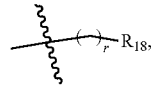

r is an integer from 1 to 6, $R_{18}$ is —COOH, —COOR$_{10}$, —OH, —OR$_{10}$, —NH$_2$, NHR$_{11}$, NR$_{11}$R$_{12}$, halogen, and $R_{10}$-$R_{12}$, are independently H or a substituted or unsubstituted $C_{1-10}$ alkyl, such as an unsubstituted $C_{1-10}$ alkyl;

$R_6$ and $R_7$ together may form a substituted or unsubstituted 3-6 membered carbocycle or a substituted or unsubstituted 4-6 membered heterocyclyl containing one or more heteroatom selected from the group consisting of O, S and N; or $R_7$ and $R_8$ together may form a substituted or unsubstituted 3-6 membered carbocycle or a substituted or unsubstituted 4-6 membered heterocyclyl containing one or more heteroatom selected from the group consisting of O, S and N; or $R_8$ and $R_9$ together may form a substituted or unsubstituted 3-6 membered carbocycle or a substituted or unsubstituted 4-6 membered heterocyclyl containing one or more heteroatom selected from the group consisting of O, S and N; or $R_6$, $R_7$, $R_8$ and $R_9$ are each independently H, OH, halogen, a substituted or unsubstituted $C_{1-10}$ alkyl, a substituted or unsubstituted $C_{1-10}$ alkoxy, a substituted or unsubstituted aryl or a substituted or unsubstituted heteroaryl;

$R_{10}$, $R_{11}$ and $R_{12}$ are each independently a substituted or unsubstituted $C_{1-10}$ alkyl;

Y is H, a substituted or unsubstituted $C_{1-10}$ alkyl, a substituted or unsubstituted aryl, or a substituted or unsubstituted aralkyl (e.g. a benzyl);

m is an integer from 0 to 10, from 0 to 8, or from 0 to 6, such as 0, 1, 2, 3, 4, 5, 6, 7, 8, 9, or 10; and n is an integer from 1 to 6, such as 1, 2, 3, 4, 5 or 6;

or an enantiomer, tautomer, stereoisomers, solvate, zwitterion, polymorph, prodrug, or a pharmaceutically acceptable salt thereof.

In some aspects of Formula I, $R_4$ and each occurrence of $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, —COOH, —COOR$_{10}$, —CH$_2$COOH; —CH$_2$COOR$_{10}$, —CH$_2$OH, —CH$_2$OR$_{10}$, —CONH$_2$, —CH$_2$NH$_2$, —CH$_2$NHR$_{11}$, —CH$_2$N$_{11}$R$_{12}$, —NCO, —CH$_2$-halogen, —CHO, —CN, —NO$_2$, —NH$_2$, —NHR$_{11}$, —NR$_{11}$R$_{12}$.

In some aspects of Formula Ib, Formula Ic, and/or Formula I, $R_6$ and $R_7$ together or $R_7$ and $R_8$ together form a substituted or unsubstituted 4-6 membered heterocyclyl containing one or more heteroatom selected from the group consisting of O, S and N. In some aspects of Formula Ib, Formula Ic, and/or Formula I, $R_6$ and $R_7$ together or $R_7$ and $R_8$ together form a substituted or unsubstituted 4-6 membered heterocyclyl containing one or more O and/or one or more N. In some aspects of Formula Ib, Formula Ic, and/or Formula I, $R_6$ and $R_7$ together or $R_7$ and $R_8$ together form a substituted or unsubstituted 5 membered heterocyclyl containing one or more O, such as two O.

In one aspect, the IDO1 small molecule inhibitors or antagonists can be a compound of Formula IIa or Formula IIb:

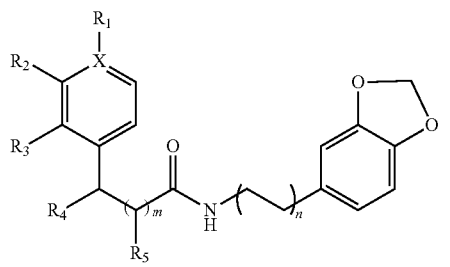

Formula IIa

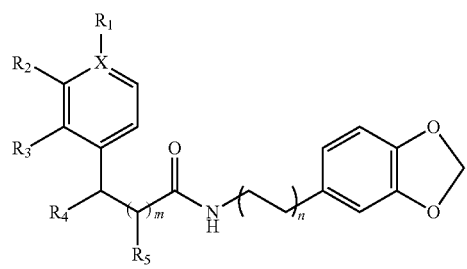

Formula IIb wherein

X is each independently C or N;

$R_1$ is independently absent, H, OH, halogen, an unsubstituted $C_{1-10}$ alkyl, or an unsubstituted $C_{1-10}$ alkoxy;

$R_2$ and $R_3$ together form a substituted or unsubstituted 3-6 membered carbocycle (e.g. an aromatic carbocycle, such as an aryl, or a saturated carbocycle, such as a cycloalkyl), or $R_2$ and $R_3$ are each independently H, OH, halogen, an unsubstituted $C_{1-10}$ alkyl, or an unsubstituted $C_{1-10}$ alkoxy;

$R_4$ and $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, —COOH, —COOR$_{10}$, —CH$_2$COOH; —CH$_2$COOR$_{10}$, —CH$_2$OH, —CH$_2$OR$_{10}$, —CONH$_2$, —CH$_2$NH$_2$, —CH$_2$NHR$_{11}$, —CH$_2$N$_{11}$R$_{12}$, —NCO, —CH$_2$-halogen, —CHO, —CN, —NO$_2$, —NH$_2$, —NHR$_{11}$, —NR$_{11}$R$_{12}$, $R_{10}$, $R_{11}$ and $R_{12}$ are each independently a substituted or unsubstituted $C_{1-10}$ alkyl;

m is an integer from 0 to 10, from 0 to 8, from 0 to 6, such as 0, 1, 2, 3, 4, 5, 6, 7, 8, 9, or 10; and n is an integer from 1 to 6, such as 1, 2, 3, 4, 5 or 6;

or an enantiomer, tautomer, stereoisomers, solvate, zwitterion, polymorph, prodrug, or a pharmaceutically acceptable salt thereof.

In some forms of Formula Ib, Formula Ic, Formula I, Formula IIa, and/or Formula IIb, the compound contains one or more stereocenters on the carbon(s) attached to $R_4$ and/or $R_5$.

In some embodiments, the compound is selected from the group consisting of

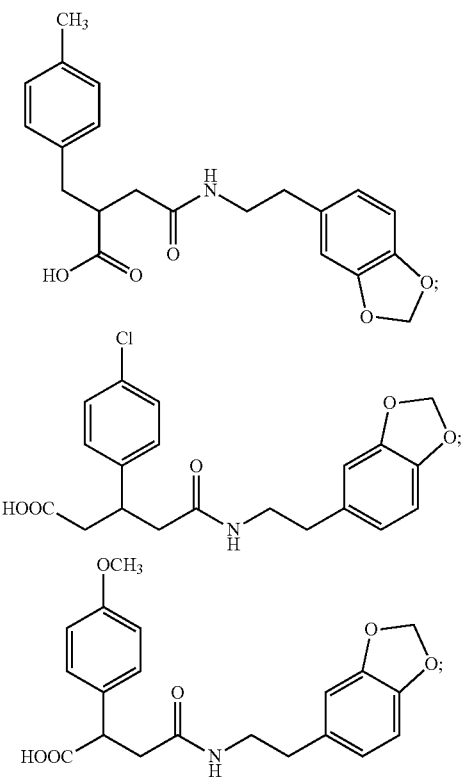

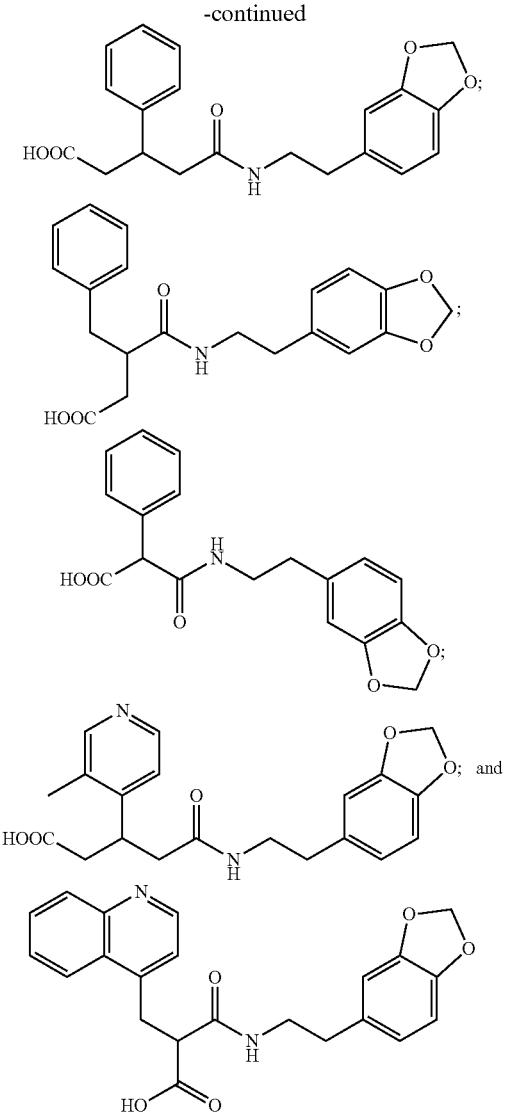

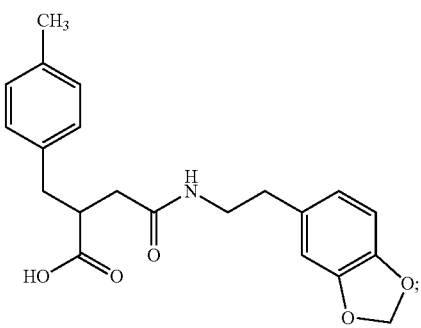

or a pharmaceutically acceptable salt thereof.

Another embodiment provides a pharmaceutical composition containing a compound according to any one of Formulae Ia, Ib, Ic, I, IIa, and IIb or a pharmaceutically acceptable salt thereof, and optionally a pharmaceutically acceptable carrier, adjuvant or vehicle. In some embodiments, the compound contained in the pharmaceutical composition is selected from the group consisting of

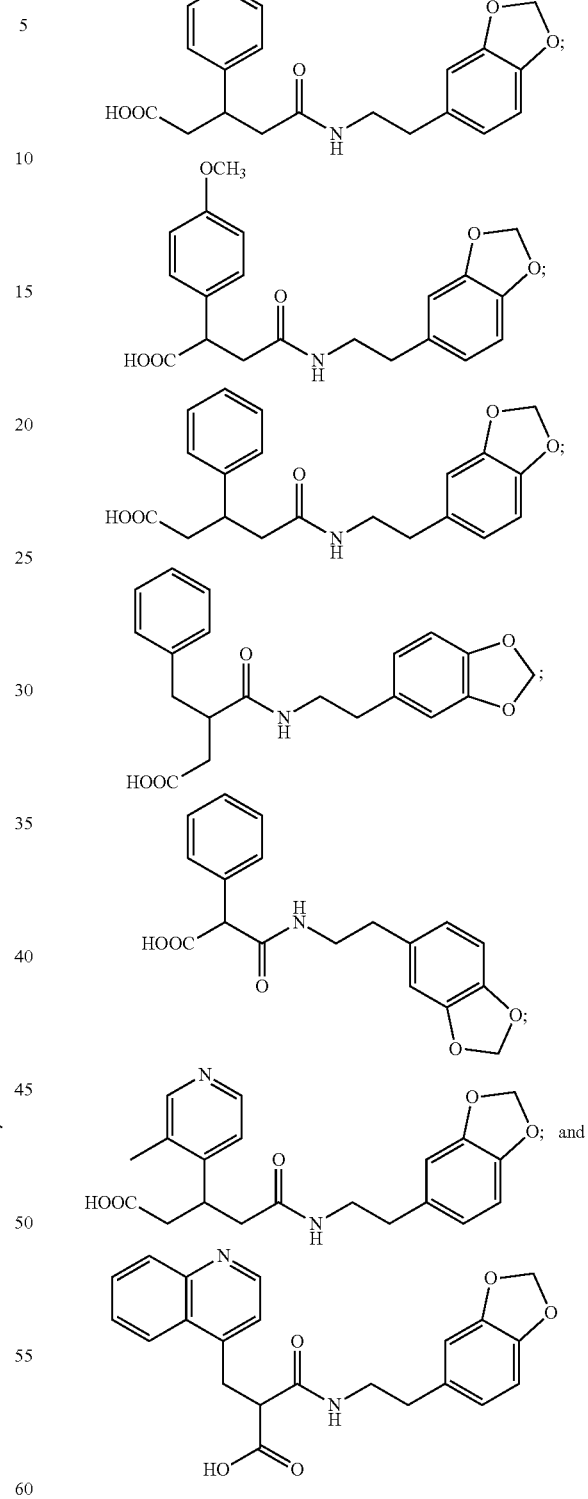

or a pharmaceutically acceptable salt thereof.

In other aspect, a process for preparing a compound of any one of Formulae Ia, Ib, Ic, I, IIa, and IIb is provided.

Another embodiment provides a method for inhibiting IDO1 in a subject in need thereof, including the step of contacting the subject's cells expressing IDO1 with a compound according to any one of Formulae Ia, Ib, Ic, I, IIa, and IIb, or a pharmaceutical composition thereof. In some embodiments, the compound used in the method for inhibiting IDO1 in the subject in need thereof is selected from the group consisting of

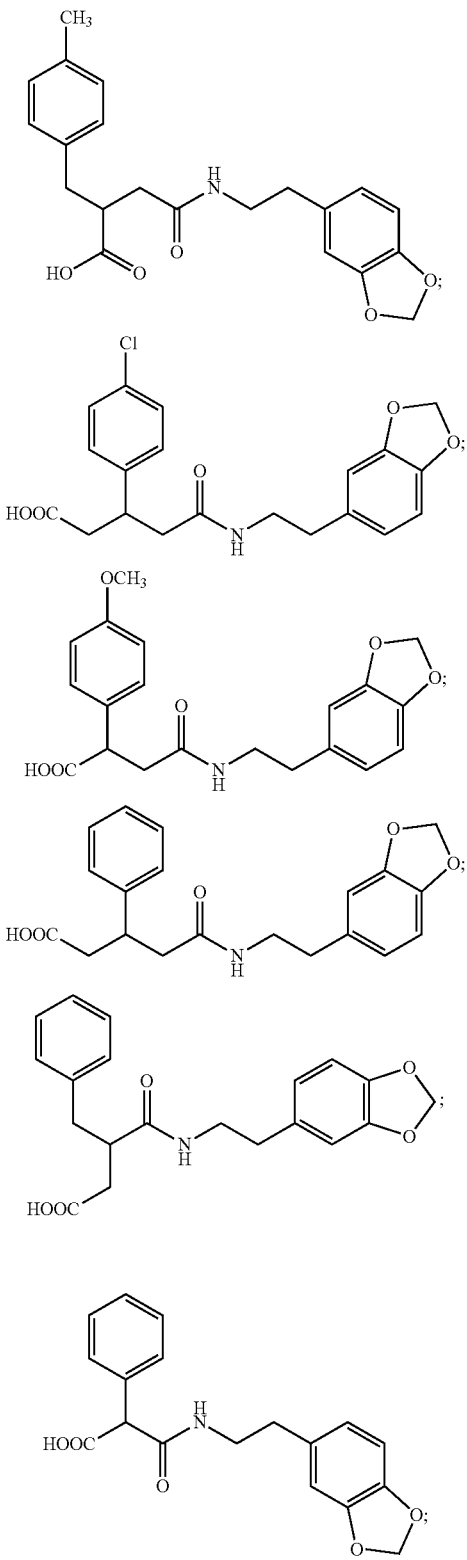

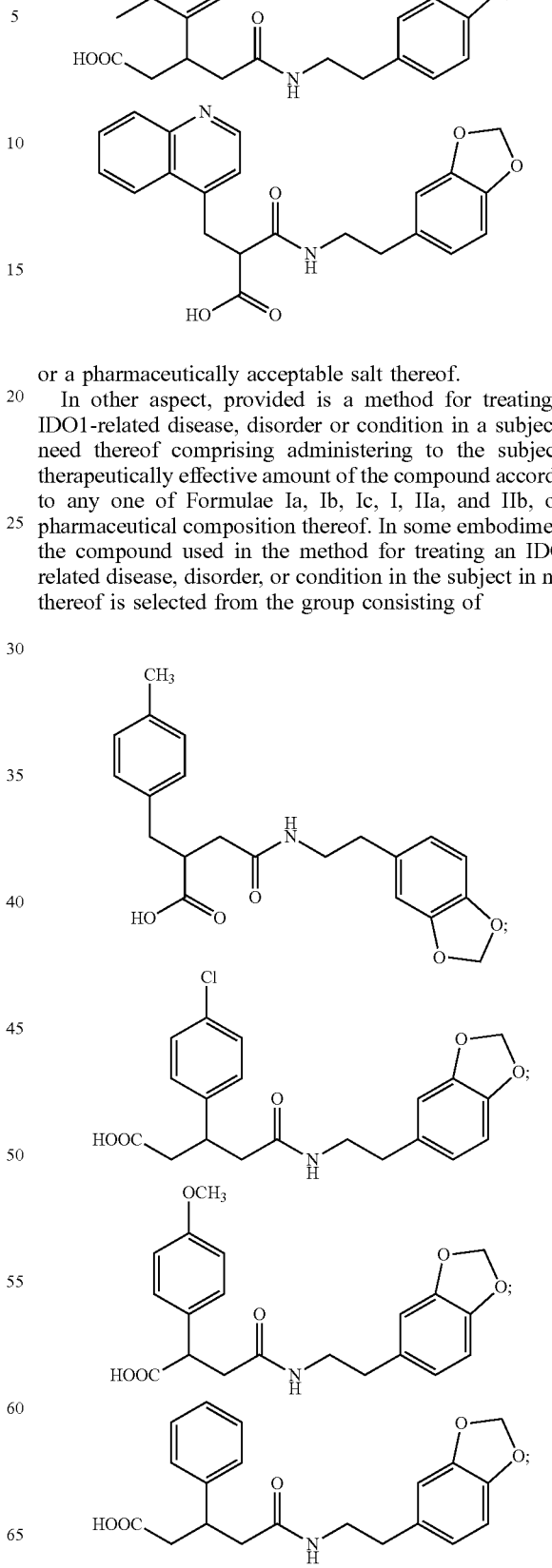

or a pharmaceutically acceptable salt thereof.

In other aspect, provided is a method for treating an IDO1-related disease, disorder or condition in a subject in need thereof comprising administering to the subject a therapeutically effective amount of the compound according to any one of Formulae Ia, Ib, Ic, I, IIa, and IIb, or a pharmaceutical composition thereof. In some embodiments, the compound used in the method for treating an IDO1-related disease, disorder, or condition in the subject in need thereof is selected from the group consisting of

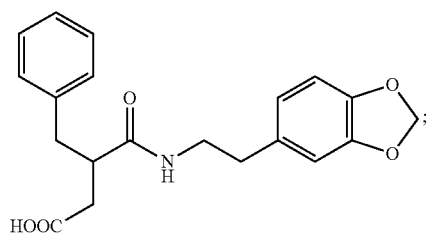

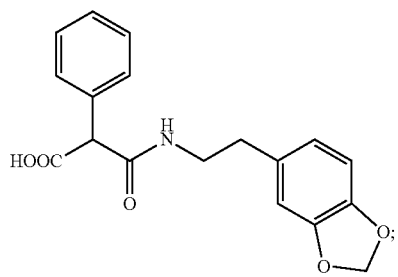

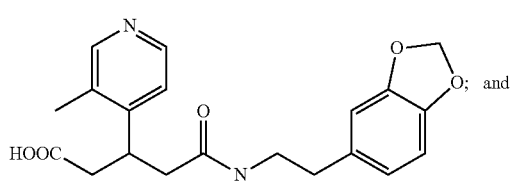

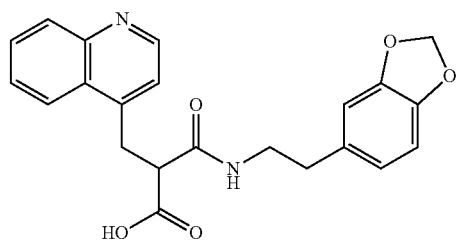

or a pharmaceutically acceptable salt thereof.

In another aspect, the IDO1-related disease, disorder or condition to be treated with the disclosed IDO antagonists is sarcopenia or age-related muscle loss.

Another embodiment provides a method for treating a sarcopenia in a subject in need thereof by administering to the subject a therapeutically effective amount of the compound according to any one of Formulae Ia, Ib, Ic, I, IIa, and IIb, or a pharmaceutical composition thereof. In some embodiments the compound used in the method for treating a saccopertia in a subject in need thereof is selected from the group consisting of

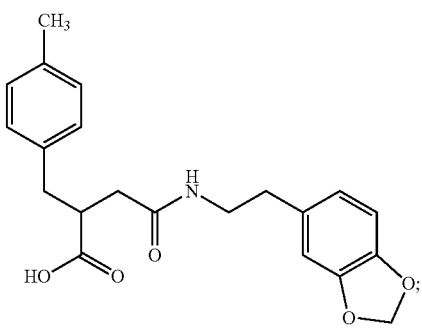

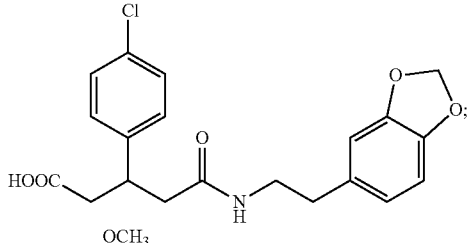

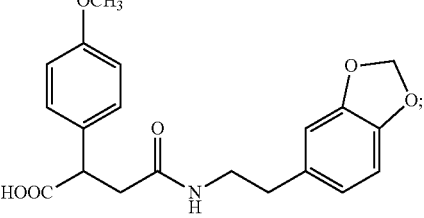

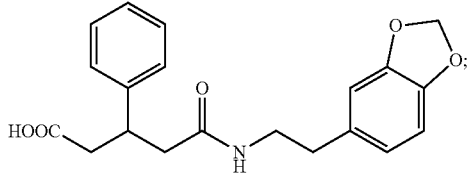

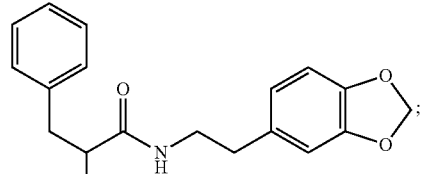

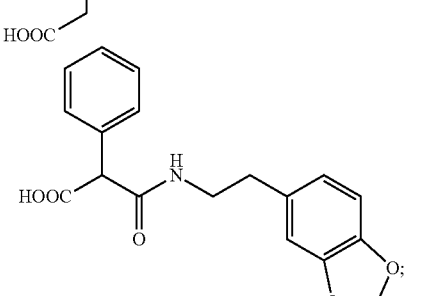

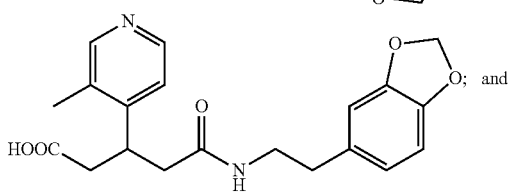

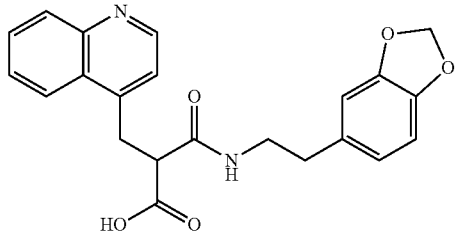

or a pharmaceutically acceptable salt thereof.

Still another embodiment provides a method for inhibiting or reducing the production of kynurenine in a subject in need thereof comprising administering to the subject an effective amount of a compound according to any one of Formulae Ia, Ib, Ic, I, IIa, and IIb, or a pharmaceutically acceptable salt or pharmaceutical composition thereof to inhibit or reduce the production of kynurenine in the subject. In some embodiments the compound used in the method for inhibiting or reducing the production of kynurenine in a subject in need thereof is selected from the group consisting of

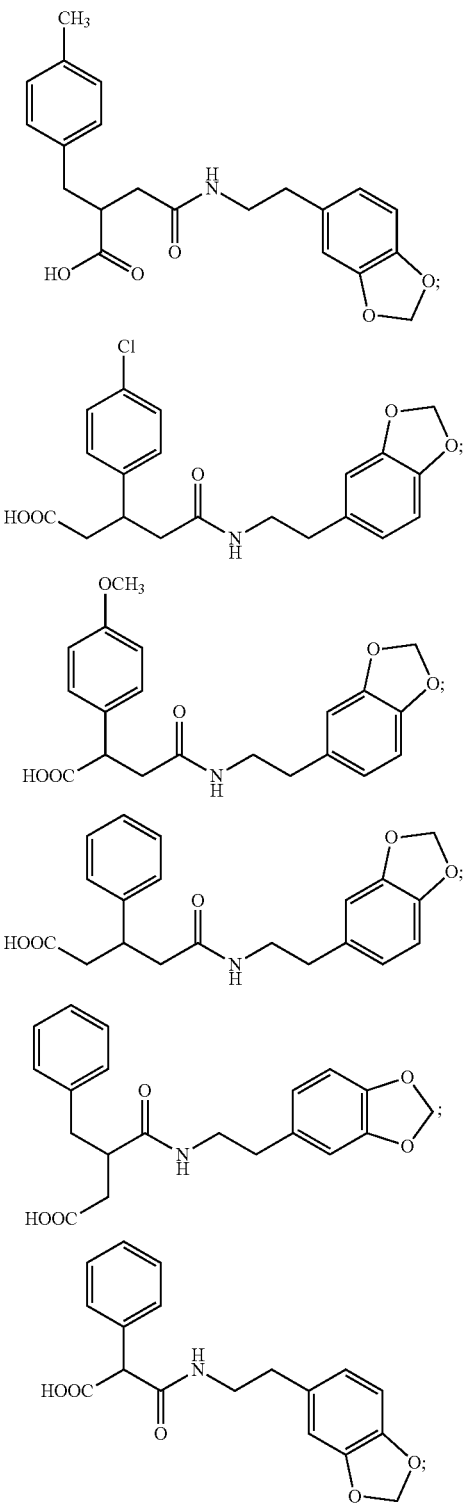

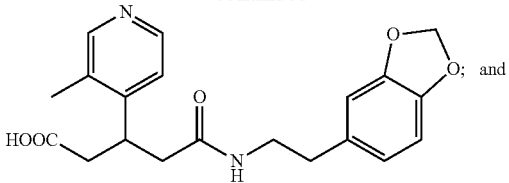

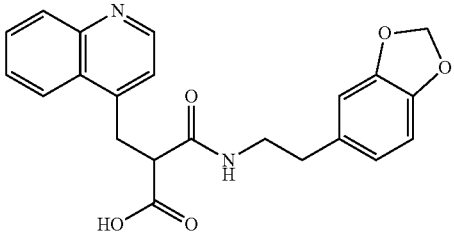

or a pharmaceutically acceptable salt thereof.

Rosmarinic acid salts such as rosmarinic acid carnitine (A), rosmarinic acid creatine (B), rosmarinic acid nicotinic acid (C), and rosmarinic acid metformin (D) are described. Products A-D can be synthesized by reacting rosmarinic acid with an equimolar amount of carnitine, creatine, nicotinic acid, or metformin under reflux in ethanol or MeCN for 3 hours. The reaction mixture can be then taken to dryness in vacuo to give an ionic liquid product A-D.

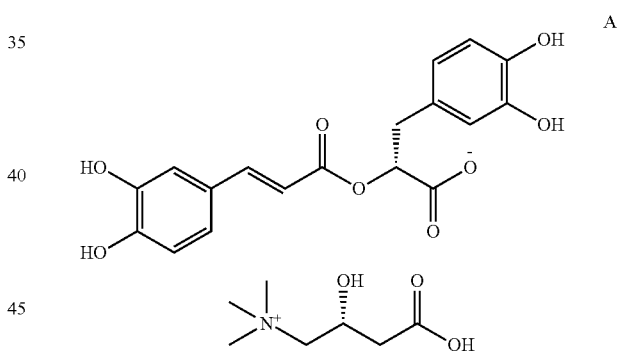

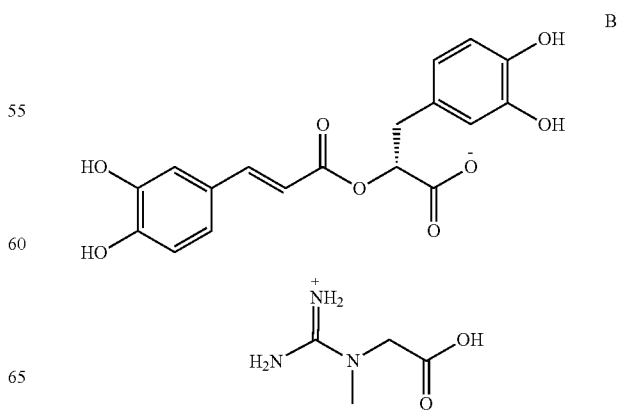

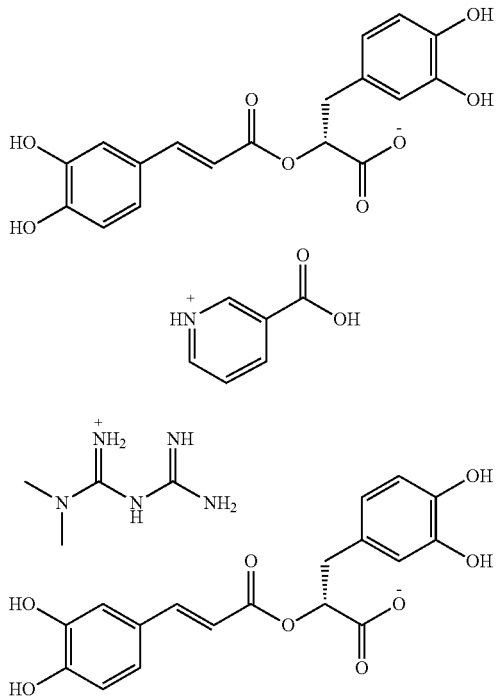

DETAILED DESCRIPTION OF THE INVENTION

I. Definitions

Figures 1A, 1B:
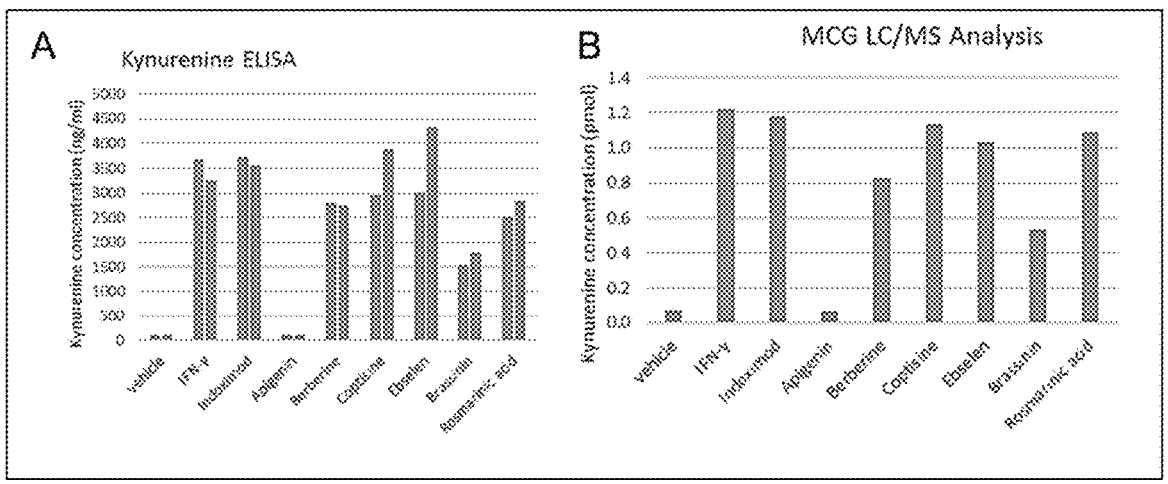
FIGS. 1A-1B show kynurenine levels in cell culture media following IDO1 inhibitor treatment, detected using Kynurenine ELISA (FIG. 1A) and LC/MS (FIG. 1B).

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms "groups" and "radicals" can be considered interchangeable when used herein.

The articles "a" and "an" may be used herein to refer to one or to more than one (i.e., at least one) of the grammatical objects of the article. By way of example "an analogue" means one analogue or more than one analogue.

As used herein, the term "pharmaceutical composition" means a mixture comprising a pharmaceutically acceptable active ingredient, in combination with suitable pharmaceutically acceptable excipients. In one embodiment the pharmaceutically acceptable ingredient is a pharmaceutically acceptable acid addition salt of the compound of formula I, or a solvate or hydrate of this acid addition salt.

Pharmaceutical excipients are substances other than the pharmaceutically acceptable active ingredient which have been appropriately evaluated for safety and which are intentionally included in an oral solid dosage form. For example, excipients can aid in the processing of the drug delivery system during its manufacture, protect, support or enhance stability, bioavailability or patient acceptability, assist in product identification, or enhance any other attribute of the overall safety, effectiveness or delivery of the drug during storage or use. Examples of excipients include, for example but without limitation inert solid diluents (bulking agent e.g., lactose), binders (e.g., starch), glidants (e.g., colloidal silica), lubricants (e.g., non-ionic lubricants such as vegetable oils), disintegrants (e.g., starch, polivinylpyrrolidone), coating better polymers (e.g., hydroxypropyl methylcellulose), colorants (e.g., iron oxide), and/or surfactants (e.g., non-ionic surfactants).

As used herein, the term "pharmaceutical formulation" means a composition in which different chemical substances, including the active drug, are combined to produce a final medicinal product. Examples of formulation include enteral formulations (tablets, capsules), parenteral formulations (liquids, lyophilized powders), or topical formulations (cutaneous, inhalable).

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of any one of Formulae Ia, Ib, Ic, I, IIa, and IIb or derivatives thereof that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. More particularly, such salts are formed with hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, or L-Tartaric acid; and (3) salts formed when a proton is removed from the parent compound, such that an anion of the compound is formed that can pair with a suitable cation to form the salt.

The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound described herein is administered.

"Solvate" refers to forms of the compound that are associated with a solvent, usually by a solvolysis reaction. This physical association includes hydrogen bonding. Conventional solvents include water, ethanol, acetic acid and the like. The compounds described herein may be prepared e.g. in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

The terms "inert solid diluent" or "solid diluent" or "diluents" refer to materials used to produce appropriate dosage form size, performance and processing properties for tablets and/or capsules. An inert solid diluent can be also referred to as filler or filler material. Particular examples of diluents include cellulose powdered, silicified microcrystalline cellulose acetate, compressible sugar, confectioner's sugar, corn starch and pregelatinized starch, dextrates, dextrin, dextrose, erythritol, ethylcellulose, fructose, fumaric acid, glyceryl palmitostearate, inhalation lactose, isomalt, kaolin, lactitol, lactose, anhydrous, monohydrate and corn starch, spray dried monohydrate and microcrystalline cellulose, maltodextrin, maltose, mannitol, medium-chain triglycerides, microcrystalline cellulose, polydextrose, polymethacrylates, simethicone, sorbitol, pregelatinized starch, sterilizable maize, sucrose, sugar spheres, sulfobutylether β-cyclodextrin, talc, tragacanth, trehalose, or xylitol. More particular examples of diluents include cellulose powdered, silicified microcrystalline cellulose acetate, compressible sugar, corn starch and pregelatinized starch, dextrose, fructose, glyceryl palmitostearate, anhydrous, monohydrate and corn starch, spray dried monohydrate and microcrystalline cellulose, maltodextrin, maltose, mannitol, medium-chain triglycerides, microcrystalline cellulose, polydextrose, sorbitol, starch, pregelatinized, sucrose, sugar spheres, trehalose, or xylitol.

"Lubricant" refers to materials that prevent or reduce ingredients from clumping together and from sticking to the tablet punches or capsule filling machine. Lubricants also ensure that tablet formation and ejection can occur with low friction between the solid and die wall. Particular examples of lubricants include canola oil, hydrogenated castor oil, cottonseed oil, glyceryl behenate, glyceryl monostearate, glyceryl palmitostearate, medium-chain triglycerides, mineral oil, light mineral oil, octyldodecanol, poloxamer, polyethylene glycol, polyoxyethylene stearates, polyvinyl alcohol, starch, or hydrogenated vegetable oil. More particular examples of diluents include glyceryl behenate, glyceryl monostearate, or hydrogenated vegetable oil.

"Disintegrant" refers to material that dissolve when wet causing the tablet to break apart in the digestive tract, releasing the active ingredients for absorption. They ensure that when the tablet is in contact with water, it rapidly breaks down into smaller fragments, facilitating dissolution. Particular examples of disintegrants include alginic acid, powdered cellulose, chitosan, colloidal silicon dioxide, corn starch and pregelatinized starch, crospovidone, glycine, guar gum, low-substituted hydroxypropyl cellulose, methylcellulose, microcrystalline cellulose, or povidone.

The term "colorant" describes an agent that imparts color to a formulation. Particular examples of colorants include iron oxide, or synthetic organic dyes (US Food and Drug administration, Code of Federal Regulations, Title 21 CFR Part73, Subpart B).

The term "plasticizing agent" or "plasticizer" refers to an agent that is added to promote flexibility of films or coatings. Particular examples of plasticizing agent include polyethylene glycols or propylene glycol.

The term "pigment" used herein refers to an insoluble coloring agent.

The term "film-coating agent" or 'coating agent' or 'coating material' refers to an agent that is used to produce a cosmetic or functional layer on the outer surface of a dosage form. Particular examples of film-coating agent include glucose syrup, maltodextrin, alginates, or carrageenan.

"Glidant" refers to materials that are used to promote powder flow by reducing interparticle friction and cohesion. These are used in combination with lubricants as they have no ability to reduce die wall friction. Particular examples of glidants include powdered cellulose, colloidal silicon dioxide, hydrophobic colloidal silica, silicon dioxide, or talc. More particular examples of glidants include colloidal silicon dioxide, hydrophobic colloidal silica, silicon dioxide, or talc.

"Flavoring agents" refers to material that can be used to mask unpleasant tasting active ingredients and improve the acceptance that the patient will complete a course of medication. Flavorings may be natural (e.g., fruit extract) or artificial. Non limiting examples of flavoring agents include mint, cherry, anise, peach, apricot, licorice, raspberry, or vanilla.

The term "subject" includes mammals such a human, a dog, a cat, a rat, a monkey, rabbits, guinea pigs, etc. The terms "human", "patient" and "subject" are used interchangeably herein.

"Effective amount" means the amount of a compound described herein that, when administered to a subject for treating a disease, is sufficient to effect such treatment for the disease. The 'effective amount' can vary depending on the compound, the disease and its severity, and the age, weight, etc., of the subject to be treated.

"Preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the compounds described herein may include isotopic variants with radioisotopes, in the instance for example, where the resulting compounds may be used for drug and/or substrate tissue distribution studies. The radioactive isotopes tritium, i.e., $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron, and 13 Emission Topography (PET) studies for examining substrate receptor occupancy.

All isotopic variants of the compounds provided herein, radioactive or not, are intended to be encompassed within the scope of the compound.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly inter-converted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

The term "alkyl" as used herein, whether used alone or as part of another group, refers to a substituted or unsubstituted aliphatic hydrocarbon chain and includes, but is not limited to, straight and branched chains containing from 1 to 20 carbon atoms, preferably from 2 to 20, from 1 to 10, from 2 to 10, from 1 to 8, from 2 to 8, from 1 to 6, from 2 to 6, from 1 to 4, from 2 to 4, from 1 to 3 carbon atoms, unless explicitly specified otherwise. Illustrative alkyl groups can include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

The term "alkenyl" as used herein, whether used alone or as part of another group, refers to a substituted or unsubstituted aliphatic hydrocarbon chain and includes, but is not limited to, straight and branched chains having 2 to 8 carbon atoms and containing at least one carbon-carbon double bond.

The term "alkynyl" as used herein, whether used alone or as part of another group, refers to a substituted or unsubstituted aliphatic hydrocarbon chain and includes, but is not limited to, straight and branched chains having 1 to 6 carbon atoms and containing at least one carbon-carbon triple bond.

The term "alkoxy" as used herein, whether used alone or as part of another group, refers to alkyl-O— wherein alkyl is hereinbefore defined.

The term "cycloalkyl" as used herein, whether used alone or as part of another group, refers to a monocyclic, bicyclic, tricyclic, fused, bridged or spiro monovalent saturated hydrocarbon moiety, wherein the carbon atoms are located inside or outside of the ring system. Any suitable ring position of the cycloalkyl moiety may be covalently linked to the defined chemical structures. Illustrative cycloalkyl groups can include, but are not limited to, cyclopropyl, cyclopropylmethyl, cyclobutyl, cyclopentyl, cyclohexyl, cyclohexylmethyl, cyclohexylethyl, cycloheptyl, norbornyl, adamantly, spiro[4,5]decanyl, and homologs, isomers and the alike.

The term "aryl" as used herein, whether used alone or as part of another group, refers to an aromatic carbocyclic ring system having 6 to 30 carbon atoms, preferably 6 to 10 carbon atoms, optionally substituted with 1 to 3 substituents independently selected from halogen, nitro cyano, hydroxy, alkyl, alkenyl, alkoxy, cycloalkyl, amino, alkylamino, dialkylamino, carboxy, alkoxycarbonyl, haloalkyl, and phenyl.

The term "phenyl" as used herein, whether used alone or as part of another group, refers to a substituted or unsubstituted phenyl group.

The term "heteroaryl" as used herein, whether used alone or as part of another group, refers to a 3 to 30 membered aryl heterocyclic ring, which contains from 1 to 4 heteroatoms selected from the group consisting of O, N, Si, P and S atoms in the ring and may be fused with a carbocyclic or heterocyclic ring at any possible position.

The term "heterocycloalkyl" as used herein, whether used alone or as part of another group, refers to a 5 to 7 membered saturated ring containing carbon atoms and from 1 to 2 heteroatoms selected from the group consisting of O, N and S atoms.

The term "halogen or halo" as used herein, refers to fluoro, chloro, bromo or iodo.

The term "haloalkyl" as used herein, whether used alone or as part of another group, refers to an alkyl as hereinbefore defined, independently substituted with 1 to 3, F, Cl, Br or I.

"Substituted," as used herein, refers to all permissible substituents of the functional groups described herein. In the broadest sense, the permissible substituents include acyclic and cyclic, branched and unbranched, carbocyclic and heterocyclic, aromatic and nonaromatic substituents of organic compounds. Illustrative sub stituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, an amino acid. Such a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, and an amino acid can be further substituted.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The term "small molecule inhibitors or antagonists" as used herein, refers to inhibitors or antagonists that have a molecular weight in a range from 0.1 kDa to 1 kDa.

The term "about" as used herein, refers that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments. Additionally, in phrase "about X to Y," is the same as "about X to about Y," that is the term "about" modifies both "X" and "Y."

The term "compound" as used herein, refers to salts, solvates, complexes, isomers, stereoisomers, diastereoisomers, tautomers, and isotopes of the compound or any combination thereof.

The term "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are used in their inclusive, open-ended, and non-limiting sense.

The term "racemic" as used herein refers to a mixture of the (+) and (−) enantiomers of a compound wherein the (+) and (−) enantiomers are present in approximately a 1:1 ratio. The terms "substantially optically pure," "optically pure," and "optically pure enantiomers," as used herein, mean that the composition contains greater than about 90% of a single stereoisomer by weight, preferably greater than about 95% of the desired enantiomer by weight, and more preferably greater than about 99% of the desired enantiomer by weight, based upon the total weight.

The term "enantiomer" refers to a stereoisomer that is a non-superimposable mirror image of each other. A diastereomer is a stereoisomer with two or more stereocenters, and the isomers are not mirror images of each other.

A hallmark of aging is the progressive decline in skeletal muscle function, characterized by reduced force generating capacity and loss of muscle mass. These phenomena, referred to collectively as sarcopenia, are common in aged humans and animal models. Moreover, age-dependent deterioration of muscle function is not restricted to mammals as it is also observed in the nematode *Caenorhabditis elegans* (*C. elegans*). It is estimated that sarcopenia affects as many as 45% of the population over the age of 60, leading to profound loss of function in the elderly. Indeed, loss of muscular strength is highly predictive of frailty, and disability, all of which cause mortality with increased age. Much attention is focused on understanding how to reverse muscle wasting, and significant advances in this field have led to early clinical trials targeting muscle growth, but there are no established treatments for age-related loss of muscle mass at this time. In contrast, improving specific force production, which is also significantly reduced in aged muscle, has received less attention. The loss of specific force suggests that the calcium-($Ca^{2+}$) dependent process known as excitation-contraction (EC) coupling may be impaired in aged muscle. During EC coupling in skeletal muscle, muscle membrane depolarization activates voltage sensing channels in the transverse tubules ($Ca_v1.1$) which in turn activate the sarcoplasmic reticulum (SR) $Ca^{2+}$ release channel, also known in skeletal muscle as the ryanodine receptor 1 (RyR1). The release of SR $Ca^{2+}$ via RyR1 raises cytoplasmic $[Ca^{2+}]_{cyt}$ leading to activation of actin-myosin cross-bridging and shortening of the sarcomere, manifesting as muscle contraction. Impaired $Ca^{2+}$ handling is associated with contractile dysfunction in heart failure and muscular dystrophy, and sarcopenic skeletal muscle is reported to have decreased SR $Ca^{2+}$ release. Thus, proper $Ca^{2+}$ handling in muscle plays a key role in normal EC coupling and specific force production. Cysteine nitrosylation (SNO) and carbonyl modifications of proteins are emerging as important cellular mediators for RyR function and $Ca^{2+}$ signaling. Excessive SNO-modification of RyR1 disrupts the interaction between RyR1 and calstabin1 (also known as FKBP12 in skeletal muscle). Loss of the RyR1/Calstabin1 interaction results in channels that leak SR $Ca^{2+}$. This leak leads to reduced SR $Ca^{2+}$ release and muscle function.

Currently, the primary treatment for sarcopenia is exercise. Specifically, resistance training or strength training—exercises that increase muscle strength and endurance with weights or resistance bands—are shown to be beneficial for both the prevention and treatment of sarcopenia. Resistance training is reported to positively influence the neuromuscular system, hormone concentrations, and protein synthesis rate. Research show that an exercise program of progressive resistance training can increase protein synthesis rates in the elderly in as little as two weeks. While this is possible for patients who are otherwise generally in good health and capable of conducting such exercise, it is not possible for a certain segment of the population to continually and properly follow an exercise regimen.

Current interventions for sarcopenia are focused on ways to increase muscle mass and/or reduce wasting of the aged muscle. This focus includes therapeutic regimens that utilize anabolic pathways such as testosterone, growth hormone, and insulin-like growth factor-1 signaling. Some trials with these anabolic regimens demonstrate modest increase in muscle growth but no increase in muscle strength or power. Inhibition of the endogenous negative regulator of myogenesis, myostatin (growth differentiation factor 8), has emerged as an attractive target for combating muscle weakness diseases as mutations in myostatin that inactivate or reduce its function lead to a dramatic increase of muscle girth in mice, dogs, and cattle. However, muscular dystrophy patients treated with an anti-myostatin recombinant human antibody, which inactivates the function of myostatin, failed to improve muscle power. Interestingly, the muscular dystrophy mouse model associated with dystrophinopathy.

It will be appreciated that compounds described herein may be metabolized to yield biologically active metabolites.

II. Inhibitors of IDO1

In some aspects, the IDO1 small molecule inhibitors or antagonists can be a compound of Formula Ia:

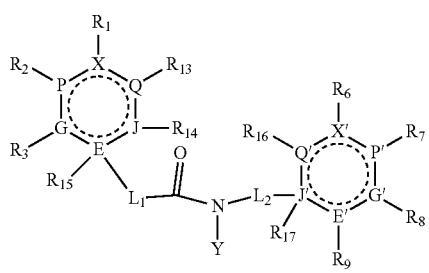

Formula Ia wherein:
X, X', P, P', Q, Q', G, G', J, J', E, and E' are independently C, N, O or S;
$R_1$-$R_3$, $R_6$-$R_9$, and $R_{13}$-$R_{17}$ are independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl, or two neighboring R groups together form a substituted or unsubstituted 3-6 membered carbocycle or substituted or unsubstituted 4-6 membered heterocyclyl containing one or more heteroatom selected from the group consisting of O, S and N;

$L_1$ and $L_2$ are independently a linker, optionally the linker is a substituted or unsubstituted $C_{1-10}$ alkyl or substituted or unsubstituted $C_{1-10}$ alkoxy; and
Y is H, a substituted or unsubstituted $C_{1-10}$ alkyl, a substituted or unsubstituted aryl, or a substituted or unsubstituted aralkyl (e.g. a benzyl);
or an enantiomer, tautomer, stereoisomers, solvate, zwitterion, polymorph, prodrug, or a pharmaceutically acceptable salt thereof.

In some aspects of Formula Ia, $L_1$ and $L_2$ are independently

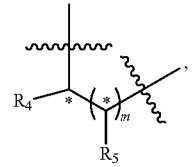

wherein m is an integer from 0 to 10; $R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

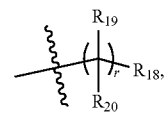

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—$COOR_{10}$, etc.), a hydroxyl, an alkoxy (—$OR_{10}$), a halogen, an amino group (e.g. a primary amino $NH_2$, a secondary amino $NHR_{11}$, or a tertiary amino $NR_{11}R_{12}$), an amide group (—$CONR_{11}R_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl. In some aspects, $R_{19}$ and $R_{20}$ are H. In some aspects, $R_{18}$ is a carbonyl (e.g., an aldehyde (—COH), a ketone, a carboxylic acid (—COOH), a carboxylate ester (—$COOR_{10}$, etc.), a hydroxyl, an alkoxy (—$OR_{10}$), a halogen, or an amino group (e.g. a primary amino $NH_2$, a secondary amino $NHR_{11}$, or a tertiary amino $NR_{11}R_{12}$).

In some aspects, the IDO1 small molecule inhibitor or antagonist contains one or more stereocenters. For example, the stereocenter is one or both of the C* in the linker $L_1$ and $L_2$ having the structure of

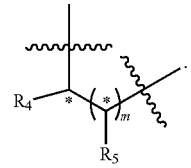

In some forms of Formula Ia, X, X', P, P', Q, Q', G, G', J, J', E, and E' are independently C or N.

In some aspects, the IDO1 small molecule inhibitors or antagonists can be a compound of Formula Ib:

Formula Ib

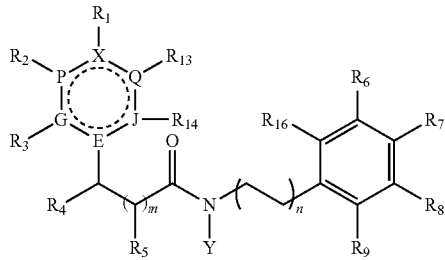

wherein:

X, P, Q, G, J, and E are independently C, N, O or S;

$R_1$-$R_3$, $R_6$-$R_9$, $R_{13}$, $R_{14}$, and $R_{16}$ are independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl, or two neighboring R groups together form a substituted or unsubstituted 3-6 membered carbocycle or substituted or unsubstituted 4-6 membered heterocyclyl containing one or more heteroatom selected from the group consisting of O, S and N;

$R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

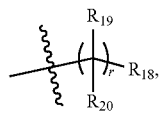

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—COOR$_{10}$, etc.), a hydroxyl, an alkoxy (—OR$_{10}$), a halogen, an amino group (e.g. a primary amino NH$_2$, a secondary amino NHR$_{11}$, or a tertiary amino NR$_{11}$R$_{12}$), an amide group (—CONR$_{11}$R$_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl;

Y is H, a substituted or unsubstituted $C_{1-10}$ alkyl, a substituted or unsubstituted aryl, or a substituted or unsubstituted aralkyl (e.g. a benzyl);

m is an integer from 0 to 10, from 0 to 8, or from 0 to 6, such as 0, 1, 2, 3, 4, 5, 6, 7, 8, 9, or 10; and n is an integer from 1 to 6, such as 1, 2, 3, 4, 5 or 6;

or an enantiomer, tautomer, stereoisomers, solvate, zwitterion, polymorph, prodrug, or a pharmaceutically acceptable salt thereof.

In some forms of Formula Ib, X, P, Q, G, J, and E are independently C or N.

In one aspect, the IDO1 small molecule inhibitors or antagonists can be a compound of Formula Ic:

Formula Ic

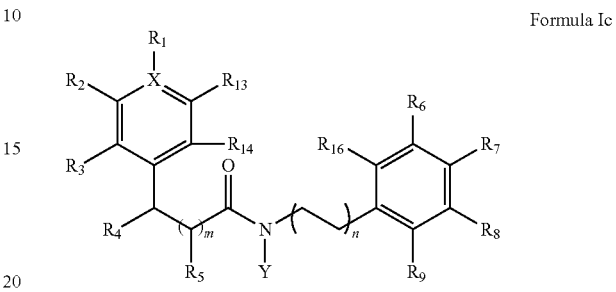

wherein:

X is C, N, O or S;

$R_1$-$R_3$, $R_6$-$R_9$, $R_{13}$, $R_{14}$, and $R_{16}$ are independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl, or two neighboring R groups together form a substituted or unsubstituted 3-6 membered carbocycle or substituted or unsubstituted 4-6 membered heterocyclyl containing one or more heteroatom selected from the group consisting of O, S and N;

$R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

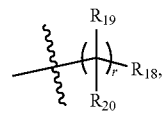

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—COOR$_{10}$, etc.), a hydroxyl, an alkoxy (—OR$_{10}$), a halogen, an amino group (e.g. a primary amino NH$_2$, a secondary amino NHR$_{11}$, or a tertiary amino NR$_{11}$R$_{12}$), an amide group (—CONR$_{11}$R$_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl;

Y is H, a substituted or unsubstituted $C_{1-10}$ alkyl, a substituted or unsubstituted aryl, or a substituted or unsubstituted aralkyl (e.g. a benzyl);

m is an integer from 0 to 10, from 0 to 8, or from 0 to 6, such as 0, 1, 2, 3, 4, 5, 6, 7, 8, 9, or 10; and n is an integer from 1 to 6, such as 1, 2, 3, 4, 5 or 6;
or an enantiomer, tautomer, stereoisomers, solvate, zwitterion, polymorph, prodrug, or a pharmaceutically acceptable salt thereof.

In some aspects of Formula Ib and Formula Ic, $R_4$ and each occurrence of $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, COOH, —COOR$_{10}$, —CONH$_2$, —NCO, —CHO, —CN, NO$_2$, NH$_2$, NHR$_{11}$, NR$_{11}$R$_{12}$, or

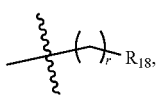

r is an integer from 1 to 6, $R_{18}$ is —COOH, —COOR$_{10}$, —OH, —OR$_{10}$, —NH$_2$, NHR$_{11}$, NR$_{11}$R$_{12}$, halogen, and $R_{10}$-$R_{12}$, are independently H or a substituted or unsubstituted $C_{1-10}$ alkyl, such as an unsubstituted $C_{1-10}$ alkyl.

In some aspects of Formula Ib and Formula Ic, $R_4$ and each occurrence of $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, COOH, —COOR$_{10}$, —CH$_2$COOH; —CH$_2$COOR$_{10}$, CH$_2$OH, —CH$_2$OR$_{10}$, —CONH$_2$, —CH$_2$NH$_2$, CH$_2$NHR$_{11}$, —CH$_2$N$_{11}$R$_{12}$, NCO, —CH$_2$-halogen, —CHO, —CN, NO$_2$, NH$_2$, NHR$_{11}$, NR$_{11}$R$_{12}$, and $R_{10}$-$R_{12}$ are independently H or a substituted or unsubstituted $C_{1-10}$ alkyl, such as an unsubstituted $C_{1-10}$ alkyl.

In some aspects of Formula Ib and/or Formula Ic, $R_2$ and $R_3$ together and/or $R_{13}$ and $R_{14}$ together form a substituted or unsubstituted 3-6 membered carbocycle or substituted or unsubstituted 4-6 membered heterocyclyl containing one or more heteroatom selected from the group consisting of O, S and N, and/or $R_{16}$ and $R_6$ together, $R_6$ and $R_7$ together, $R_7$ and $R_8$ together, and/or $R_8$ and $R_9$ together, form a substituted or unsubstituted 3-6 membered carbocycle or substituted or unsubstituted 4-6 membered heterocyclyl containing one or more heteroatom selected from the group consisting of O, S and N.

In some aspects of Formula Ib and/or Formula Ic, $R_2$ and $R_3$ together form a substituted or unsubstituted 3-6 membered carbocycle or substituted or unsubstituted 4-6 membered heterocyclyl containing one or more heteroatom selected from the group consisting of O, S and N. In some aspects of Formula Ib and/or Formula Ic, $R_6$ and $R_7$ together or $R_7$ and $R_8$ together form a substituted or unsubstituted 3-6 membered carbocycle or substituted or unsubstituted 4-6 membered heterocyclyl containing one or more heteroatom selected from the group consisting of O, S and N. In some aspects of Formula Ib and/or Formula Ic, $R_2$ and $R_3$ together form a substituted or unsubstituted 3-6 membered carbocycle or substituted or unsubstituted 4-6 membered heterocyclyl containing one or more heteroatom selected from the group consisting of O, S and N, and/or $R_6$ and $R_7$ together or $R_7$ and $R_8$ together form a substituted or unsubstituted 3-6 membered carbocycle or substituted or unsubstituted 4-6 membered heterocyclyl containing one or more heteroatom selected from the group consisting of O, S and N.

One aspect provides a compound of Formula I:

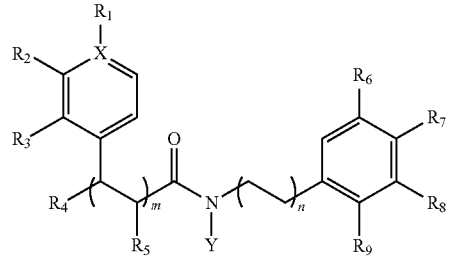

wherein
X is each independently C, CH or N;
$R_1$ is independently absent, H, OH, halogen, a substituted or unsubstituted $C_{1-10}$ alkyl, a substituted or unsubstituted $C_{1-10}$ alkoxy, a substituted or unsubstituted $C_{3-10}$ cycloalkyl, a substituted or unsubstituted aryl, or a substituted or unsubstituted heteroaryl;
$R_2$ and $R_3$ together form a substituted or unsubstituted 3-6 membered carbocycle or a substituted or unsubstituted 4-6 membered heterocyclyl containing one or more heteroatom selected from the group consisting of O, S and N; or
$R_2$ and $R_3$ are each independently H, OH, halogen, a substituted or unsubstituted $C_{1-10}$ alkyl, a substituted or unsubstituted $C_{1-10}$ alkoxy, a substituted or unsubstituted aryl or a substituted or unsubstituted heteroaryl;
$R_4$ and each occurrence of $R_5$ is independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, a carbonyl (e.g., an aldehyde, a ketone, a carboxylic acid, a carboxylate ester, etc.), an amino group, an amide group, a haloalkyl, a nitro group, a nitrile group, a cyanate, an isocyanate, or

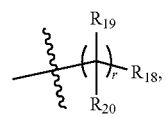

r is an integer from 1 to 6, from 1 to 5, from 1 to 4, from 1 to 3, from 1 to 2, or 1, $R_{18}$ is a carbonyl (e.g., an aldehyde (—COH), a ketone, a carboxylic acid (—COOH), a carboxylate ester (—COOR$_{10}$, etc.), a hydroxyl, an alkoxy (—OR$_{10}$), a halogen, an amino group (e.g. a primary amino NH$_2$, a secondary amino NHR$_{11}$, or a tertiary amino NR$_{11}$R$_{12}$), an amide group (—CONR$_{11}$R$_{12}$), a nitro group, a nitrile group, $R_{19}$ and $R_{20}$ are independently H or a substituted or unsubstituted $C_{1-10}$ alkyl, and $R_{10}$, $R_{11}$ and $R_{12}$ are independently H or a substituted or unsubstituted $C_{1-10}$ alkyl, such as an unsubstituted $C_{1-10}$ alkyl;
$R_6$ and $R_7$ together may form a substituted or unsubstituted 3-6 membered carbocycle or a substituted or unsubstituted 4-6 membered heterocyclyl containing one or more heteroatom selected from the group consisting of O, S and N; or
$R_7$ and $R_8$ together may form a substituted or unsubstituted 3-6 membered carbocycle or a substituted or unsubstituted 4-6 membered heterocyclyl containing one or more heteroatom selected from the group consisting of O, S and N; or $R_8$ and $R_9$ together may form a substituted or unsubstituted 3-6 membered carbocycle or a substituted or unsubstituted 4-6 membered heterocyclyl containing one or more heteroatom selected from the group consisting of O, S and N; or $R_6$, $R_7$, $R_8$ and $R_9$ are each independently H, OH, halogen, a substituted or unsubstituted $C_{1-10}$ alkyl, a substituted or unsubstituted $C_{1-10}$ alkoxy, a substituted or unsubstituted aryl or a substituted or unsubstituted heteroaryl;

m is an integer from 0 to 10, from 0 to 8, or from 0 to 6, such as 0, 1, 2, 3, 4, 5, 6, 7, 8, 9, or 10;

n is an integer from 1 to 6, such as 1, 2, 3, 4, 5 or 6; and

Y is H, a substituted or unsubstituted $C_{1-10}$ alkyl, a substituted or unsubstituted aryl, or a substituted or unsubstituted aralkyl (e.g. a benzyl);

or an enantiomer, tautomer, stereoisomers, solvate, zwitterion, polymorph, prodrug, or a pharmaceutically acceptable salt thereof.

In some aspects of Formula I, $R_4$ and each occurrence of $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, COOH, —COOR$_{10}$, —CONH$_2$, —NCO, —CHO, —CN, NO$_2$, NH$_2$, NHR$_{11}$, NR$_{11}$R$_{12}$, or

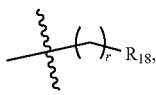

r is an integer from 1 to 6, $R_{18}$ is —COOH, —COOR$_{10}$, —OH, —OR$_{10}$, —NH$_2$, NHR$_{11}$, NR$_{11}$R$_{12}$, halogen, and $R_{10}$-$R_{12}$, are independently H or a substituted or unsubstituted $C_{1-10}$ alkyl, such as an unsubstituted $C_{1-10}$ alkyl.

In some aspects of Formula I, $R_4$ and each occurrence of $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, COOH, —COOR$_{10}$, CH$_2$COOH; —CH$_2$COOR$_{10}$, CH$_2$OH, —CH$_2$OR$_{10}$, —CONH$_2$, —CH$_2$NH$_2$, CH$_2$NHR$_{11}$, —CH$_2$N$_{11}$R$_{12}$, NCO, —CH$_2$-halogen, —CHO, —CN, NO$_2$, NH$_2$, NHR$_{11}$, NR$_{11}$R$_{12}$, and $R_{10}$-$R_{12}$ are independently H or a substituted or unsubstituted $C_{1-10}$ alkyl, such as an unsubstituted $C_{1-10}$ alkyl.

In some aspects of Formula Ib, Formula Ic, and/or Formula I, $R_6$ and $R_7$ together or $R_7$ and $R_8$ together form a substituted or unsubstituted 4-6 membered heterocyclyl containing one or more heteroatom selected from the group consisting of O, S and N. In some aspects of Formula Ib, Formula Ic, and/or Formula I, $R_6$ and $R_7$ together or $R_7$ and $R_8$ together form a substituted or unsubstituted 4-6 membered heterocyclyl containing one or more O and/or one or more N. In some aspects of Formula Ib, Formula Ic, and/or Formula I, $R_6$ and $R_7$ together or $R_7$ and $R_8$ together form a substituted or unsubstituted 5 membered heterocyclyl containing one or more O, such as two O.

In other embodiments, $R_1$ is H, a substituted or unsubstituted $C_{1-10}$ alkyl (e.g. an unsubstituted $C_{1-10}$ alkyl), a substituted or unsubstituted $C_{1-10}$ alkoxy, or halogen.

In another embodiments, $R_2$ and $R_3$ are H, a substituted or unsubstituted $C_{1-10}$ alkyl (e.g. an unsubstituted $C_{1-10}$ alkyl), a substituted or unsubstituted $C_{1-10}$ alkoxy, or $R_2$ and $R_3$ together form a substituted or unsubstituted 6 membered aryl ring.

In some embodiment, $R_4$ and each occurrence of $R_5$ are independently H, —COOH, —COOR$_{10}$, or

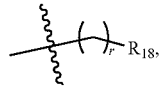

r is an integer from 1 to 6, $R_{18}$ is —COOH or —COOR$_{10}$, and $R_{10}$ is independently H or a substituted or unsubstituted $C_{1-10}$ alkyl, such as an unsubstituted $C_{1-10}$ alkyl. In some embodiment, $R_4$ and each occurrence of $R_5$ are independently H, COOH or CH$_2$COOH.

In other embodiment, $R_6$ and $R_7$ together form a substituted or unsubstituted 5 membered heterocyclyl containing one or more O, such as an unsubstituted 5 membered heterocyclyl containing one or more O.

In another embodiment, $R_7$ and $R_8$ together form a substituted or unsubstituted 5 membered heterocyclyl containing one or more O, such as an unsubstituted 5 membered heterocyclyl containing one or more O.

In further embodiment, $R_8$ and $R_9$ together form a substituted or unsubstituted 5 membered heterocyclyl containing one or more O, such as an unsubstituted 5 membered heterocyclyl containing one or more O.

In other embodiment, X is CH or N.

In one aspect, the IDO1 small molecule inhibitors or antagonists can be a compound of Formula IIa or Formula IIb:

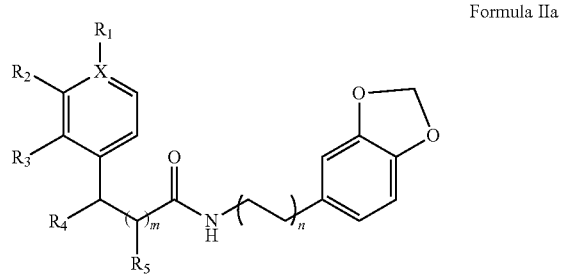

Formula IIa

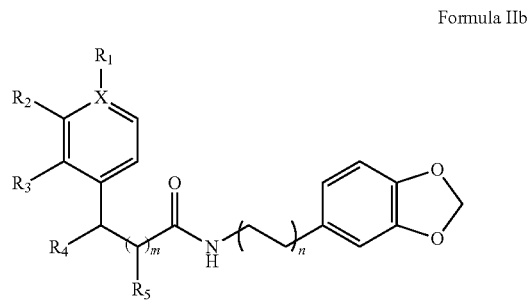

Formula IIb wherein

X is each independently C or N;

$R_1$ is independently absent, H, OH, halogen, an unsubstituted $C_{1-10}$ alkyl, or an unsubstituted $C_{1-10}$ alkoxy;

$R_2$ and $R_3$ together form a substituted or unsubstituted 3-6 membered carbocycle (e.g. an aromatic or a saturated carbocycle), or $R_2$ and $R_3$ are each independently H, OH, halogen, an unsubstituted $C_{1-10}$ alkyl, or an unsubstituted $C_{1-10}$ alkoxy;

$R_4$ and $R_5$ are independently H, OH, halogen, a substituted or unsubstituted $C_{1-10}$ alkyl, a substituted or unsubstituted $C_{1-10}$ alkoxy, a substituted or unsubstituted aryl, a substituted or unsubstituted heteroaryl, —COOH, —COOR$_{10}$, —CH$_2$COOH; —CH$_2$COOR$_{10}$, —CH$_2$OH, —CH$_2$OR$_{10}$, —CONH$_2$, —CH$_2$NH$_2$, —CH$_2$NHR$_{11}$, —CH$_2$N$_{11}$R$_{12}$, —NCO, —CH$_2$-halogen, —CHO, —CN, —NO$_2$, —NH$_2$, —NHR$_{11}$, —NR$_{11}$R$_{12}$, R$_{10}$, R$_{11}$ and R$_{12}$ are each independently a substituted or unsubstituted $C_{1-10}$ alkyl (e.g. an unsubstituted $C_{1-10}$ alkyl);

m is an integer from 0 to 10, from 0 to 8, or from 0 to 6, such as 0, 1, 2, 3, 4, 5, 6, 7, 8, 9, or 10; and n is an integer from 1 to 6, such as 1, 2, 3, 4, 5 or 6;

or an enantiomer, tautomer, stereoisomers, solvate, zwitterion, polymorph, prodrug, or a pharmaceutically acceptable salt thereof.

In some aspects of Formula Ia, Ib, Formula Ic, Formula I, Formula IIa, and/or Formula IIb, the compound contains one or more stereocenters on the carbon(s) attached to R$_4$ and/or R$_5$. The compounds of any one of Formula Ib, Formula Ic, Formula I, Formula IIa, and Formula IIb may contain one or more chiral centers or may otherwise be capable of existing as multiple stereoisomers. These may be pure (single) stereoisomers or mixtures of stereoisomers, such as enantiomers, diastereomers, and enantiomerically or diastereomerically enriched mixtures. The compounds may be capable of existing as geometric isomers. Accordingly, it is to be understood that the compounds can be pure geometric isomers or mixtures of geometric isomers.

In some aspects, for any one of Formula Ia, Ib, Ic, I, IIa, and IIb, the $C_{1-10}$ alkyl, $C_{1-10}$ alkoxy, $C_{3-10}$ cycloalkyl, aryl, and/or heteroaryl are unsubstituted $C_{1-10}$ alkyl, $C_{1-10}$ alkoxy, $C_{3-10}$ cycloalkyl, aryl, and/or heteroaryl. For any one of Formula Ia, Ib, Ic, I, IIa, and IIb, the $C_{3-10}$ cycloalkyl can be either monocyclic or polycyclic.

For any one of Formula Ia, Ib, Ic, I, IIa, and IIb, the alkyl can be a linear substituted or unsubstituted alkyl or a branched substituted or unsubstituted alkyl, such as a linear unsubstituted alkyl or a branched unsubstituted alkyl. Exemplary alkyl include a linear substituted or unsubstituted $C_1$-$C_{10}$ alkyl, a branched substituted or unsubstituted $C_4$-$C_{10}$ alkyl, a linear substituted or unsubstituted $C_1$-$C_6$ alkyl, a branched substituted or unsubstituted $C_4$-$C_6$ alkyl, a linear substituted or unsubstituted $C_1$-$C_4$ alkyl, such as a linear substituted or unsubstituted $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, or $C_1$-$C_2$ alkyl group or a branched substituted or unsubstituted $C_3$-$C_9$, $C_3$-$C_9$, $C_3$-$C_8$, $C_3$-$C_7$, $C_3$-$C_6$, $C_3$-$C_5$, or $C_3$-$C_4$ alkyl group.

For any of Formulae Ia, Ib, Ic, I, IIa, and IIb, the aryl group can be a $C_5$-$C_{30}$ aryl, a $C_5$-$C_{20}$ aryl, a $C_5$-$C_{12}$ aryl, a $C_5$-$C_{11}$ aryl, a $C_5$-$C_9$ aryl, a $C_6$-$C_{20}$ aryl, a $C_6$-$C_{12}$ aryl, a $C_6$-$C_{11}$ aryl, or a $C_6$-$C_9$ aryl; and the heteroaryl can be a $C_5$-$C_{30}$ heteroaryl, a $C_5$-$C_{20}$ heteroaryl, a $C_5$-$C_{12}$ heteroaryl, a $C_5$-$C_{11}$ heteroaryl, a $C_5$-$C_9$ heteroaryl, a $C_6$-$C_{30}$ heteroaryl, a $C_6$-$C_{20}$ heteroaryl, a $C_6$-$C_{12}$ heteroaryl, a $C_6$-$C_{11}$ heteroaryl, or a $C_6$-$C_9$ heteroaryl. For any of Formulae Ia, Ib, Ic, I, IIa, and IIb, the aryl group can be a polyaryl group, such as a $C_{10}$-$C_{30}$ polyaryl, a $C_{10}$-$C_{20}$ polyaryl, a $C_{10}$-$C_{12}$ polyaryl, a $C_{10}$-$C_{11}$ polyaryl, or a $C_{12}$-$C_{20}$ polyaryl. For any of Formulae Ia, Ib, Ic, I, IIa, and IIb, the heteroaryl group can be a polyheteroaryl, such as a $C_{10}$-$C_{30}$ polyheteroaryl, a $C_{10}$-$C_{20}$ polyheteroaryl, a $C_{10}$-$C_{12}$ polyheteroaryl, a $C_{10}$-$C_{11}$ polyheteroaryl, or a $C_{12}$-$C_{20}$ polyheteroaryl.

In some embodiments, the compound is selected from the group consisting of

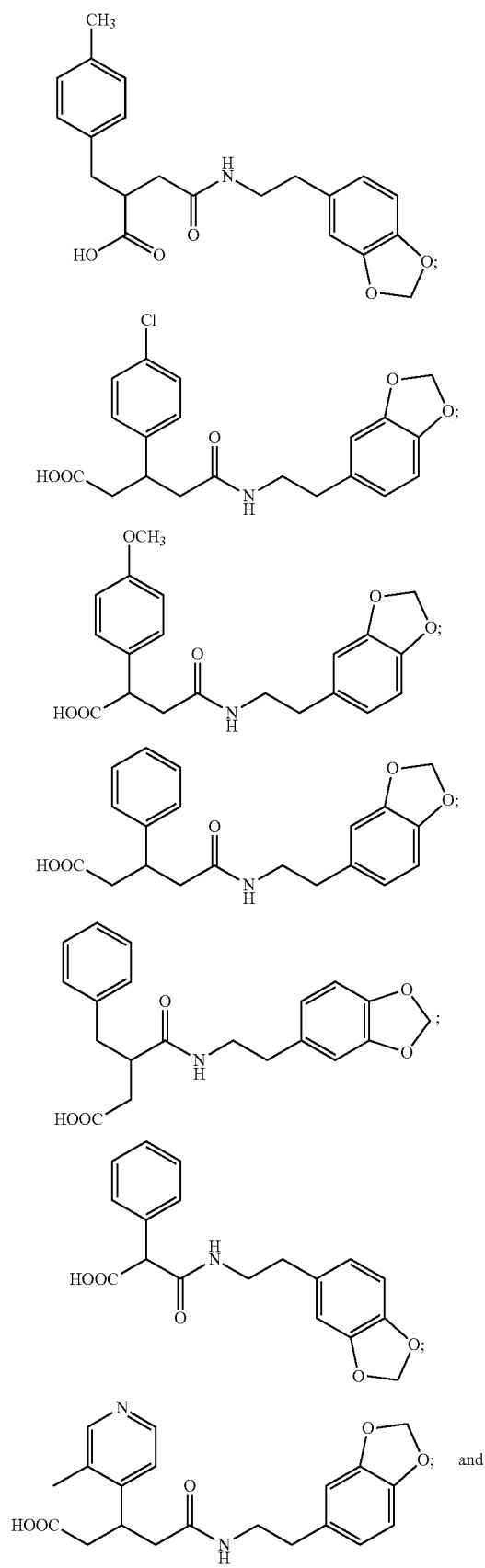

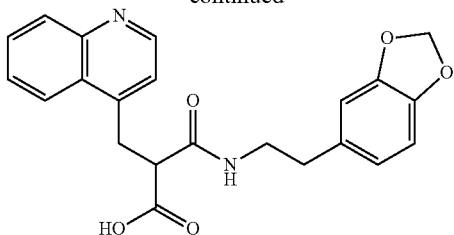

or a pharmaceutically acceptable salt thereof.

When the compounds of any one of Formulae Ia, Ib, Ic, I, IIa, and IIb, and the exemplary compounds described above are in the form of pharmaceutically acceptable salts, the compounds can be the anion or the cation of the salt. In some aspects, when in the form of a pharmaceutically acceptable salt, the compound is the anion of the salt. Anionic forms of the compounds can be formed by dissociation of one or more functional group of the compound. For example, an anionic form of the compound is formed by dissociation of a hydroxyl and/or carboxylic acid group of the compound, such that a —O⁻ and/or —COO⁻ is formed. Anionic forms of the compounds can pair with any suitable cations to form the salt, such as ammonium, iminium, metal cations, etc. In some aspects, when in the form of a pharmaceutically acceptable salt, the compound is the cation of the salt. Cationic forms of the compounds can be formed by adding a proton on one or more functional group and/or atoms of the compound. For example, a cationic form of the compound is formed by adding a proton on an amino and/or imino group of the compound, such that an ammonium and/or iminium is formed. Cationic forms of the compounds may also be formed by removing one or more electrons from an atom (e.g. oxygen) of the compound. Cationic forms of the compounds can pair with any suitable anions to form the salt, such as halide ions, phosphate, sulfate, etc.

Another embodiment provides a process for preparing a compound of any one of Formulae Ia, Ib, Ic, I, IIa, and IIb. In some embodiments the compound is selected from the group consisting of

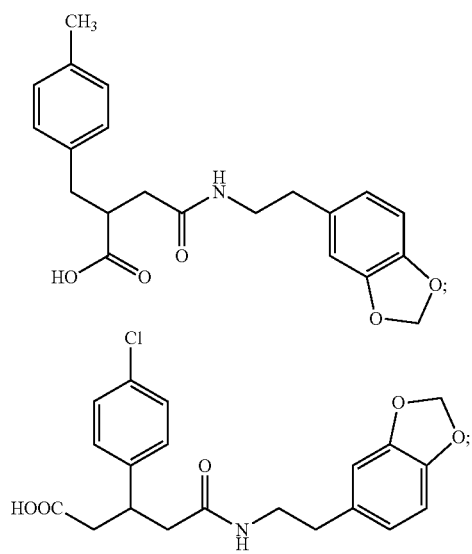

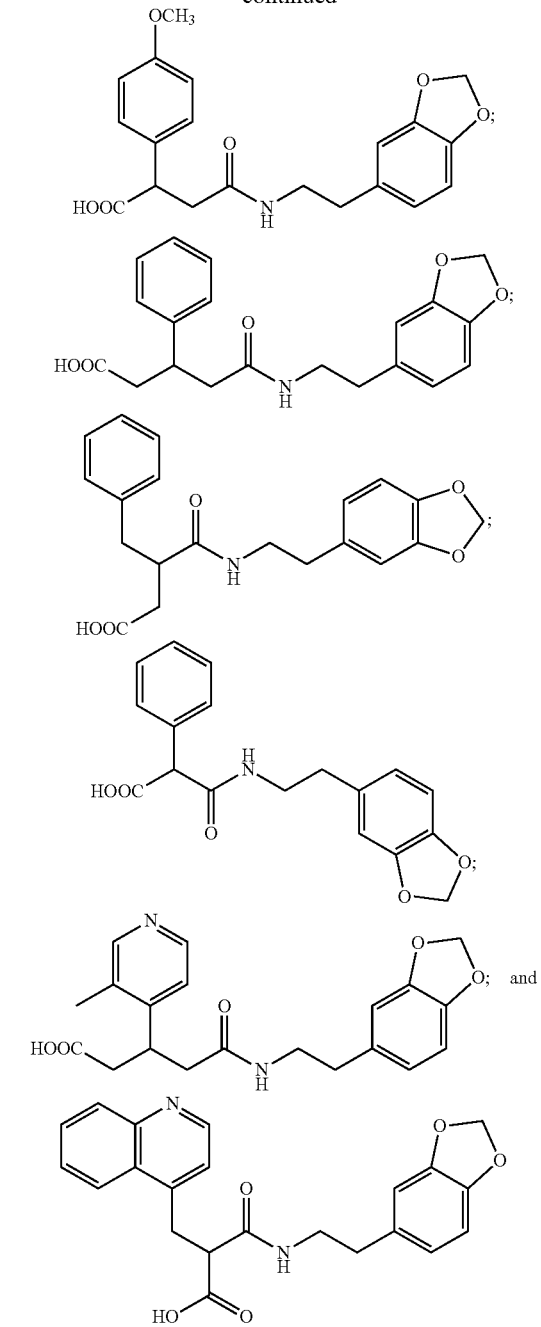

or a pharmaceutically acceptable salt thereof.

Generally, the compounds described herein can be synthesized by performing a coupling reaction between a first building block containing acyl halide or carboxylic acid and a second building block containing amines. Selecting suitable reaction conditions (e.g. reaction temperature, reaction time period, pressure, activating agent, solvent, etc.) for the coupling reaction is known. For example, synthesis of the compounds described herein includes conjugating equimolar quantities of a first building block containing carboxylic acid and a second building block containing amine using isobutyl chloroformate as an activating agent for the carboxylic acid of the first building block. The reaction mixture was then taken to dryness and the product was isolated using column chromatography.

Protecting groups for either building blocks may be used as needed and when used, a deprotection step takes place after the coupling reaction has been completed. Selecting and adding a suitable protecting group for the building blocks and performing deprotection to remove the protecting group are known.

An exemplary coupling reaction for synthesizing the compound of Formula Ia is shown below:

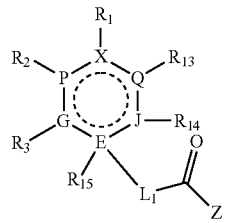

Formula Ia-1

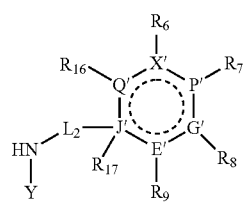 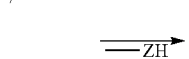

Formula Ia-2

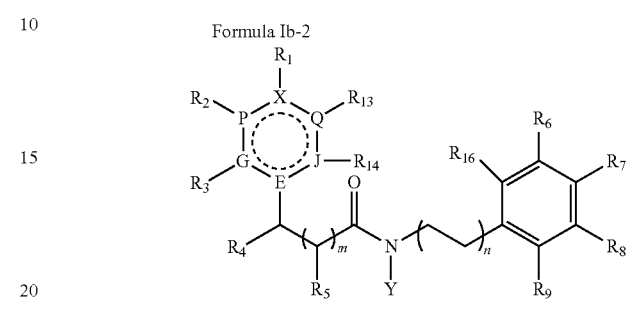

Formula Ia wherein X, X', P, P', Q, Q', G, G', J, J', E, and E'; $R_1$-$R_3$, $R_6$-$R_9$, and $R_{13}$-$R_{17}$; $L_1$ and $L_2$; and Y are as defined above for Formula Ia; and Z is a halogen (e.g. Cl, Br, or I) or OH.

An exemplary coupling reaction for synthesizing the compound of Formula Ib is shown below:

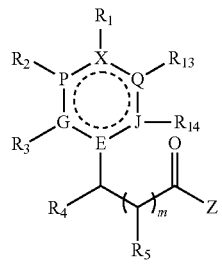

Formula Ib-1

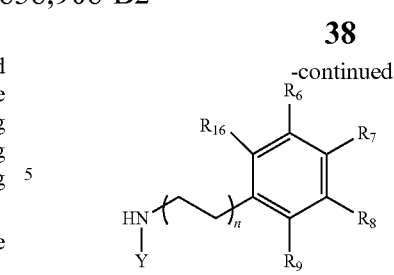

Formula Ib-2

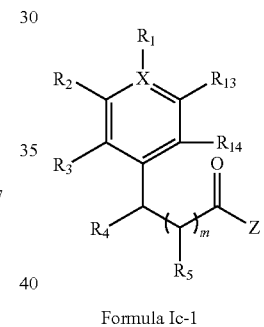

Formula Ib wherein X, P, Q, G, J, and E; $R_1$-$R_9$, $R_{13}$, $R_{14}$, and $R_{16}$; Y; m; and n are as defined above for Formula Ib; and Z is a halogen (e.g. Cl, Br, or I) or OH.

An exemplary coupling reaction for synthesizing the compound of Formula Ic is shown below:

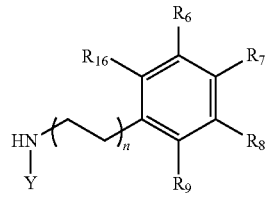

Formula Ic-1

Formula Ic-2

Formula Ic wherein X; $R_1$-$R_9$, $R_{13}$, $R_{14}$, and $R_{16}$; Y; m; and n are as defined above for Formula Ic; and Z is a halogen (e.g. Cl, Br, or I) or OH.

An exemplary coupling reaction for synthesizing the compound of Formula I is shown below:

An exemplary coupling reaction for synthesizing the compound of Formula IIa or Formula IIb is shown below:

wherein X; $R_1$-$R_5$; m; and n are as defined above for Formula I; and Z is a halogen (e.g. Cl, Br, or I) or OH.

III. Pharmaceutical Formulations

The compounds of any one of Formulae Ia, Ib, Ic, I, IIa, and IIb and combinations thereof can be formulated into a pharmaceutical composition. In some embodiments, the compounds contained in the pharmaceutical composition are selected from the group consisting of wherein X; $R_1$-$R_9$; Y; m; and n are as defined above for Formula I; and Z is a halogen (e.g. Cl, Br, or I) or OH.

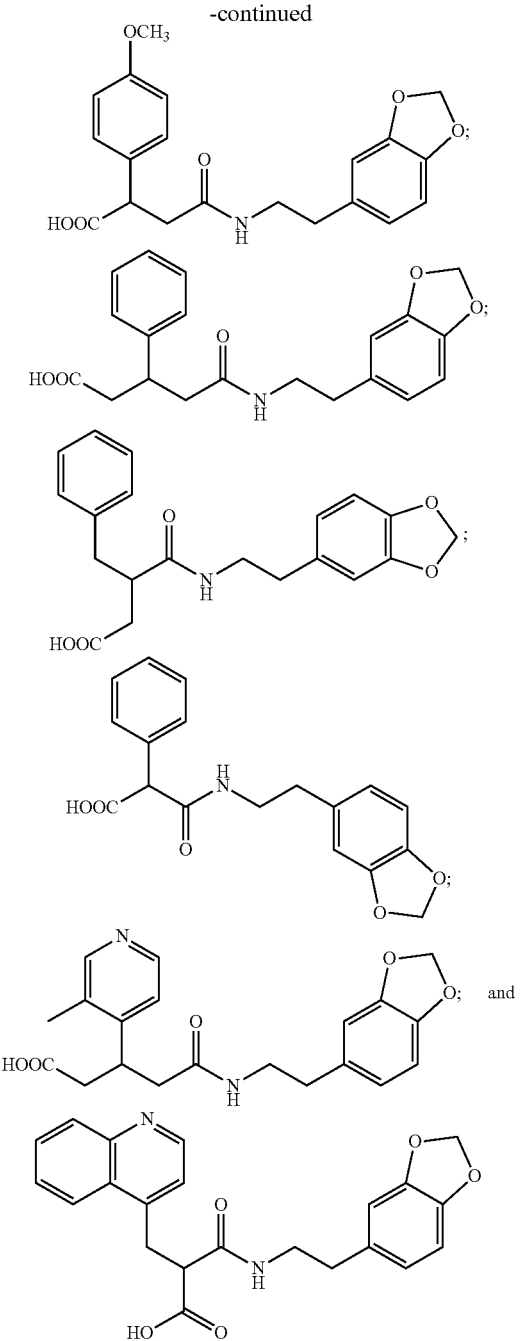

or a pharmaceutically acceptable salt thereof.

The disclosed pharmaceutical compositions can be formulated for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration. The compositions can be administered systemically.

In one embodiment, the compounds of any one of Formulae Ia, Ib, Ic, I, IIa, and IIb can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g., as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

In some embodiments, the disclosed formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. Al. (New York, Marcel Dekker, Inc., 1989), "Remington—The science and practice of pharmacy", $20^{th}$ ed., Lippincott Williams & Wilkins, Baltimore, MD, 2000, and "Pharmaceutical dosage forms and drug delivery systems", $6^{th}$ Edition, Ansel et. al., (Media, PA: Williams and Wilkins, 1995) which provides information on carriers, materials, equipment and process for preparing tablets and capsules and delayed release dosage forms of tablets, capsules, and granules.

In one embodiment, the compounds of any one of Formulae Ia, Ib, Ic, I, IIa, and IIb can be administered to a subject with or without the aid of a delivery vehicle. Appropriate delivery vehicles for the compounds are known in the art and can be selected to suit the particular active agent. For example, in some embodiments, the active agent(s) is/are incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the compounds of any one of Formulae Ia, Ib, Ic, I, IIa, and IIb. In some embodiments, release of the compounds according to any one of Formulae Ia, Ib, Ic, I, IIa, and IIb is controlled by diffusion of the compounds out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before all of the first agent is released. In still other embodiments, both agents are released at the same time over the same period of time or over different periods of time.

A. Formulations for Parenteral Administration

In one embodiment, compounds of any one of Formulae Ia, Ib, Ic, I, IIa, and IIb and pharmaceutical compositions thereof can be administered in an aqueous solution, by parenteral injection. The formulation may also be in the form of a suspension or emulsion. In general, pharmaceutical compositions are provided including effective amounts of the compound(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

B. Oral Immediate Release Formulations

Another embodiment provides suitable oral dosage forms containing of the compounds of Formula I that include but are not limited to tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

In some embodiments, binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

In some embodiments, lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

In some embodiments, stabilizers are used to inhibit or retard drug decomposition reactions which include, by way of example, oxidative reactions.

Some embodiments include surfactants. The surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

C. Extended Release Dosage Forms

One embodiment provides extended release formulations of compounds of any one of Formulae Ia, Ib, Ic, I, IIa, and IIb that are generally prepared as diffusion or osmotic systems, for example, as described in "Remington—The science and practice of pharmacy" ($20^{th}$ ed., Lippincott Williams & Wilkins, Baltimore, MD, 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations of the compounds of any one of Formulae Ia, Ib, Ic, I, IIa, and IIb can be prepared using osmotic systems or by applying a semipermeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

D. Delayed Release Dosage Forms

In some embodiments delayed release formulations of compounds of any one of Formulae Ia, Ib, Ic, I, IIa, and IIb are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

E. Formulations for Mucosal and Pulmonary Administration

The compounds of any one of Formulae Ia, Ib, Ic, I, IIa, and IIb and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the compounds of any one of Formulae Ia, Ib, Ic, I, IIa, and IIb are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

One embodiment provides for nasal delivery for administration of the compounds of formula I.

The compounds of any one of Formulae Ia, Ib, Ic, I, IIa, and IIb can be formulated as an aerosol. The term aerosol refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated.

Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

F. Topical and Transdermal Formulations

Transdermal formulations containing the compounds of any one of Formulae Ia, Ib, Ic, I, IIa, and IIb may also be prepared. These will typically be gels, ointments, lotions, sprays, or patches, all of which can be prepared using standard technology. Transdermal formulations can include penetration enhancers.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol.

The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophillic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ® 721 (stearyl poly (21) oxyethylene ether) (ICI Americas Inc. Corp.). Chemical penetrations and methods of increasing transdermal drug delivery are described in Inayat, et al., *Tropical Journal of Pharmaceutical Research,* 8 (2):173-179 (2009) and Fox, et al., *Molecules,* 16:10507-10540

(2011). In some embodiments, the penetration enhancer is, or includes, an alcohol such ethanol, or others disclosed herein or known in the art.

Delivery of drugs by the transdermal route has been known for many years. Advantages of a transdermal drug delivery compared to other types of medication delivery such as oral, intravenous, intramuscular, etc., include avoidance of hepatic first pass metabolism, ability to discontinue administration by removal of the system, the ability to control drug delivery for a longer time than the usual gastrointestinal transit of oral dosage form, and the ability to modify the properties of the biological barrier to absorption.

Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Usually, reservoir patches include a porous membrane covering the reservoir of medication which can control release, while heat melting thin layers of medication embedded in the polymer matrix (e.g., the adhesive layer), can control release of drug from matrix or monolithic devices. Accordingly, the active agent can be released from a patch in a controlled fashion without necessarily being in a controlled release formulation.

Patches can include a liner which protects the patch during storage and is removed prior to use; drug or drug solution in direct contact with release liner; adhesive which serves to adhere the components of the patch together along with adhering the patch to the skin; one or more membranes, which can separate other layers, control the release of the drug from the reservoir and multi-layer patches, etc., and backing which protects the patch from the outer environment.

Common types of transdermal patches include, but are not limited to, single-layer drug-in-adhesive patches, wherein the adhesive layer contains the drug and serves to adhere the various layers of the patch together, along with the entire system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for control release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described in U.S. Pat. Nos. 6,461,644, 6,676,961, 5,985,311, and 5,948,433.

In some embodiments, the composition is formulated for transdermal delivery and administered using a transdermal patch. In some embodiments, the formulation, the patch, or both are designed for extended release of the curcumin conjugate.

Exemplary symptoms, pharmacologic, and physiologic effects are discussed in more detail below.

G. Methods of Manufacture

As will be appreciated by those skilled in the art and as described in the pertinent texts and literature, a number of methods are available for preparing formulations containing the compounds of Formula I including but not limited to tablets, beads, granules, microparticle, or nanparticles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, PA: Williams & Wilkins, 1995).

An exemplary method for preparing extended release tablets includes compressing a drug-containing blend, e.g., blend of drug-containing granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

IV. Methods of Use

The compounds of any one of Formulae Ia, Ib, Ic, I, IIa, and IIb or N-(2-benzo[1,3]dioxol-5-yl-ethyl)-2-(4-methylbenzyl)-succinamic acid and pharmaceutical compositions thereof are useful for the treatment of an IDO1-related disease, disorder or condition in a subject in need thereof. Generally, the method includes administering to the subject a therapeutically effective amount of the compound disclosed herein or N-(2-benzo[1,3]dioxol-5-yl-ethyl)-2-(4-methyl-benzyl)-succinamic acid or a pharmaceutical composition thereof to treat the IDO1-related disease, disorder or condition. The subject can be a mammal, such as humans, dogs, cats, mice, rats, monkeys, rabbits, guinea pigs, or agricultural animals such as cattle, sheep, pigs, etc.

In some embodiments, the IDO1-related disease, disorder or condition treated using the methods disclosed herein is age related muscle loss or sarcopenia, wherein the compound or pharmaceutical composition thereof is administered in an effective amount to treat or prevent the age-related muscle loss or sarcopenia. In some embodiments, the IDO1-related disease, disorder or condition treated using the method disclosed herein is muscle loss related to systemic inflammation (e.g. cancer and/or HIV-induced muscle wasting), wherein the compound or pharmaceutical composition thereof is administered in an effective amount to treat or prevent the muscle loss related to systemic inflammation. For example, the IDO1-related disease, disorder or condition treated using the method disclosed herein is cancer-induced muscle wasting (cachexia) wherein the compound or pharmaceutical composition thereof is administered in an effective amount to treat or prevent the muscle wasting. For example, the IDO1-related disease, disorder or condition treated using the method disclosed herein is HIV-induced muscle wasting (including HIV before/under/after treatment with antiretroviral therapy), wherein the compound or pharmaceutical composition thereof is administered in an effective amount to treat or prevent the muscle wasting.

In some embodiments, a compound is administered in an effective amount to treat an age-related disorder using the method disclosed herein. One disorder of particular importance is frailty. Frailty is a syndrome that can be characterized by loss of reserve, feebleness, vulnerability, and failure of homeostasis (Chan, *The Hong Kong Medical Diary*, 13 (9):7-9 (2008)). The loss of reserve and resilience is part of a feed-forward loop inviting associated comorbidities leading to further decreasing reserve. It is believed that declines in the molecular, cellular and physiological systems of the aging body are the underlying mechanisms associated with the reduction in the effectiveness of muscle and bone as well as declines in the circulatory, hormonal, and immune systems that are typical of frail individuals (Fried, et al., *Journal of Gerontology: Medical Sciences*, 56A (3):M146-156 (2001), and Chan, *The Hong Kong Medical Diary*, 13 (9):7-9 (2008)). Frailty can be the consequence of one or more additional underlying diseases, for example cachexia, immobilization, aging, chronic disease, or cancer.

Although frailty, like many other age-related diseases, is often associated with chronological age, not all elderly individuals are frail and not all frail individuals are elderly. Frail individuals are typically at an increased risk of disability and death from minor internal stresses such as anxiety and depression, or external stresses such physical strain, infections, heat, and cold. For example, individuals suffering from frailty can exhibit one or more symptoms including sarcopenia, unintentional non-muscle weight loss greater than 10 lbs per week, decreased grip strength, low energy expenditure, weakness, fatigue, and decreased walking time. These factors can contribute to a progressive increase in disability, dependency, the need for long term care, and mortality in frail individuals over time (Chan, *The Hong Kong Medical Diary*, 13 (9):7-9 (2008)).

In some embodiments, the subject suffers from a disease or condition such as muscle atrophy, muscular dystrophy, sarcopenia, frailty, or combinations thereof. The disclosed compositions and methods can be used to treat or prevent muscle atrophy, muscular dystrophy, sarcopenia, frailty, combinations thereof, or one or more symptoms or comorbidities thereof, wherein the compound is administered in an effective amount to treat or prevent one or more of these diseases or conditions. The muscle atrophy or sarcopenia can result from cachexia, immobilization, aging, chronic disease, cancer, or combinations thereof. The disclosed compositions and methods can also be used to treat or prevent muscle loss related to systemic inflammation, such as muscle wasting (cachexia) induced by cancer and HIV (including HIV being treated with antiretroviral therapy). Another embodiment provides methods for inhibiting IDO1 in a subject in need thereof by contacting the subject's cells expressing IDO1 with an effective amount of a compound of any one of Formulae Ia, Ib, Ic, I, IIa, and IIb or N-(2-benzo [1,3]dioxol-5-yl-ethyl)-2-(4-methyl-benzyl)-succinamic acid or a pharmaceutical composition thereof to inhibit IDO1 in the subject. In some aspects, the methods for inhibiting IDO1 in a subject in need thereof includes contacting the subject's cells expressing IDO1 with an effective amount of a compound of any one of Formulae Ia, Ib, Ic, I, IIa, and IIb or a pharmaceutical composition thereof to inhibit IDO1 in the subject. In some aspects, the methods for inhibiting IDO1 in a subject in need thereof includes contacting the subject's cells expressing IDO1 with an effective amount of N-(2-benzo[1,3]dioxol-5-yl-ethyl)-2-(4-methyl-benzyl)-succinamic acid or a pharmaceutical composition thereof to inhibit IDO1 in the subject. In one embodiment, the compound used in the method for inhibiting IDO1 in the subject in need thereof is selected from the group consisting of

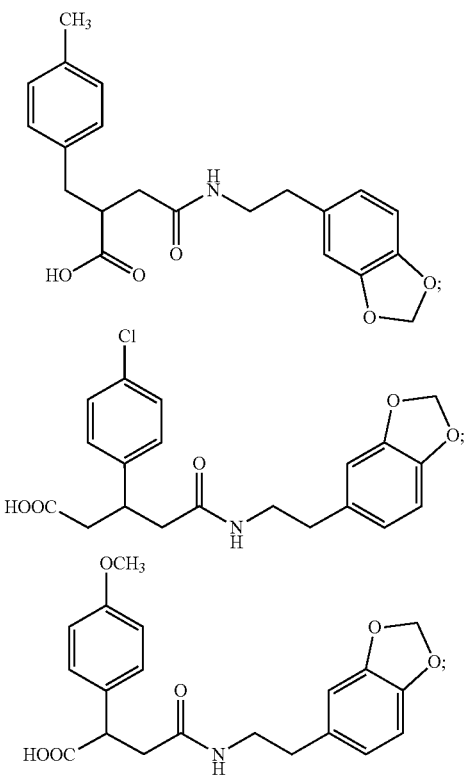

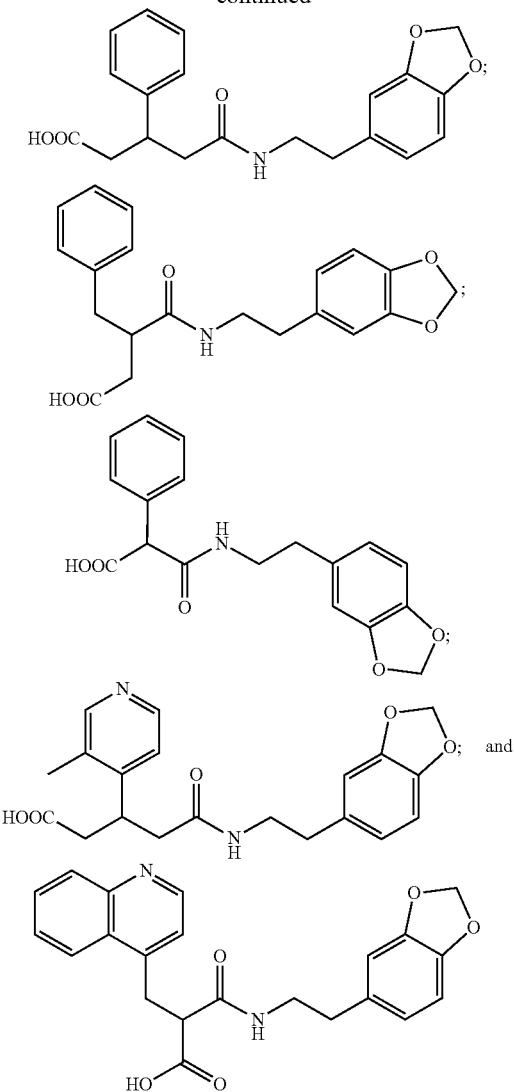

or a pharmaceutically acceptable salt thereof.

Another embodiment provides a method for treating a sarcopenia in a subject in need thereof by administering to the subject a therapeutically effective amount of the compound according to any one of Formulae Ia, Ib, Ic, I, IIa, and IIb or a pharmaceutical composition thereof to treat sarcopenia. Sarcopenia typically refers to the loss of skeletal muscle mass associated with advancing age (Cruz-Jentoft, A. et al., *Age and Aging*, 39:412-423 (2010); Lang, T. et al., *Osteoporosis Int*, 21:543-559 (2010)). Loss of skeletal muscle mass can also be unrelated to age. For example, loss of skeletal muscle mass occurs in subjects with cachexia. In some embodiments the compound is selected from the group consist of still another embodiment provides a method for inhibiting or reducing the production of kynurenine in a subject in need thereof comprising administering to the subject an effective amount of a compound according to any one of Formulae Ia, Ib, Ic, I, IIa, and IIb or a pharmaceutically acceptable salt or pharmaceutical composition thereof to inhibit or reduce the production of kynurenine in the subject. In some aspects, using the method disclosed herein, an effective amount of the compounds according to any one of Formulae Ia, Ib, Ic, I, IIa, and IIb or a pharmaceutically acceptable salt or pharmaceutical composition thereof is administered to lower kynurenine or other downstream tryptophan metabolite levels. In some embodiments the compound used in the method for inhibiting or reducing the production of kynurenine in the subject in need thereof is selected from the group consisting of

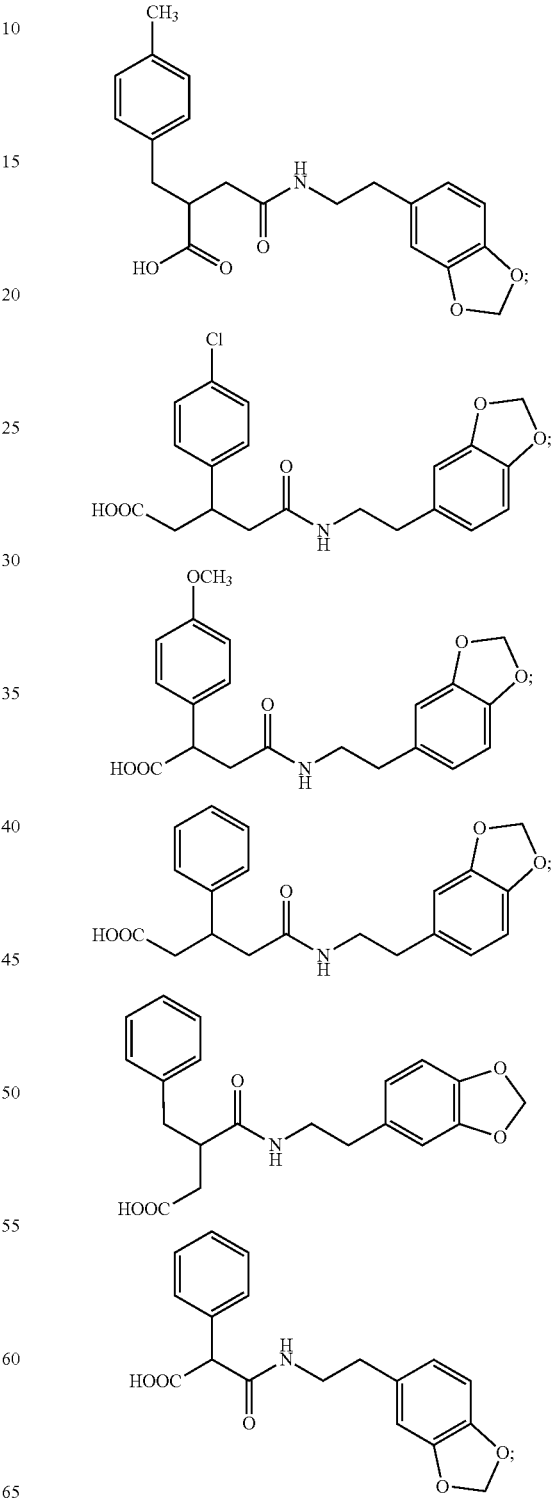

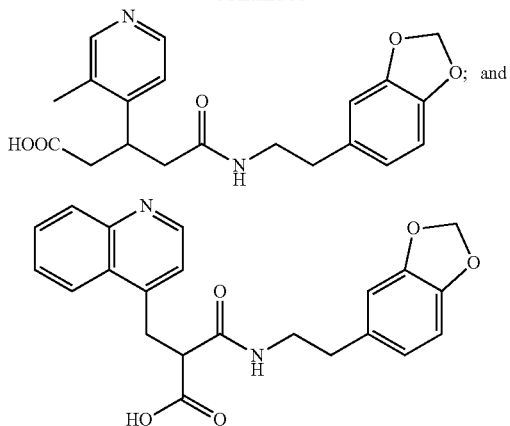

or a pharmaceutically acceptable salt thereof.

Another embodiment provides a method for inhibiting or reducing the production of kynurenine in a subject in need thereof comprising administering to the subject an effective amount of a compound according to any one of Formulae Ia, Ib, Ic, I, IIa, and IIb or N-(2-benzo[1,3]dioxol-5-yl-ethyl)-2-(4-methyl-benzyl)-succinamic acid or a pharmaceutically acceptable salt or pharmaceutical composition thereof to inhibit or reduce the production of kynurenine in the subject. In some aspects, the method for inhibiting or reducing the production of kynurenine in a subject in need thereof comprising administering to the subject an effective amount of a compound according to any one of Formulae Ia, Ib, Ic, I, IIa, and IIb or a pharmaceutically acceptable salt or pharmaceutical composition thereof to inhibit or reduce the production of kynurenine in the subject. In some embodiments the compound used in the method for inhibiting or reducing the production of kynurenine in the subject in need thereof is selected from the group consisting of

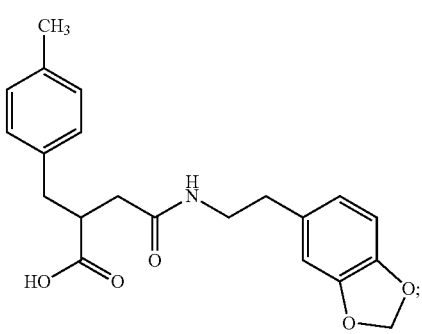

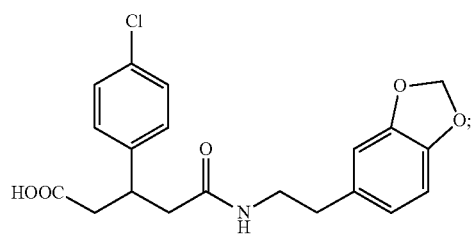

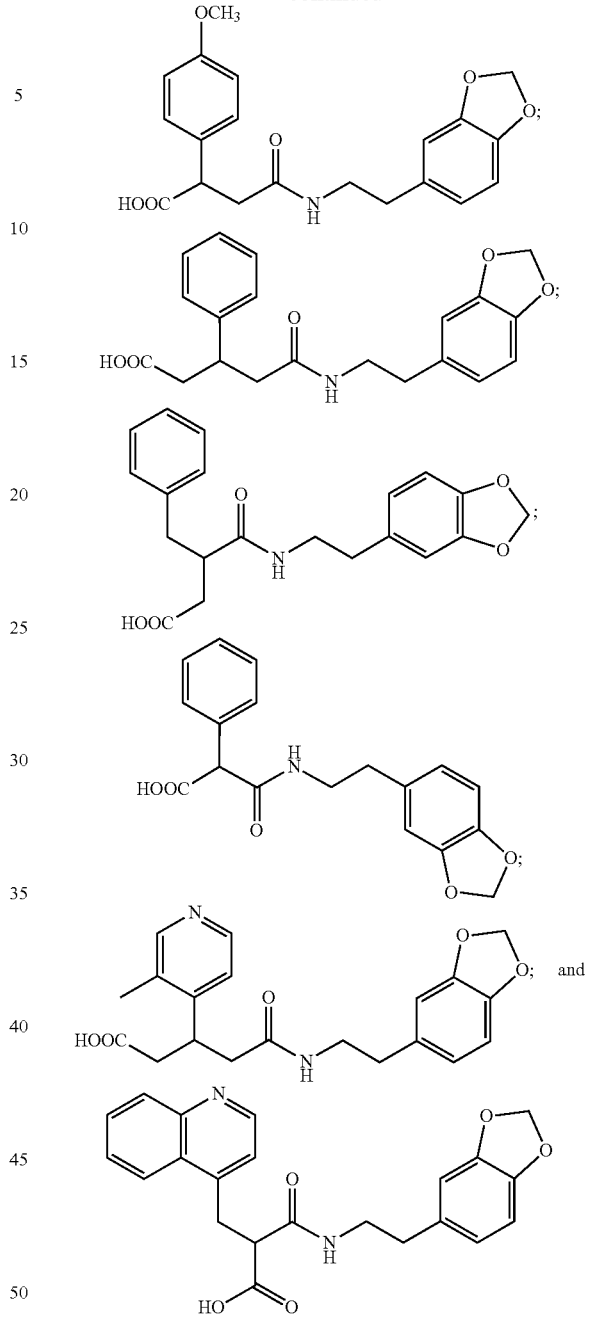

or a pharmaceutically acceptable salt thereof.

In some embodiments, the disclosed compounds are administered in combination with one or more additional therapeutic agents. The combination of active agents can be administered in the same or different admixture. The combination of active agents can be administered at concurrently or sequential. Current treatments for many age-related disorders, including frailty are generally limited to treating the physical symptoms of the disease. For example, frail individuals may be encouraged to increase their amount of exercise and dietary intake, which can induce weight gain, increase mobility, enhance physical performance, improve gait, improve balance, increase bone mineral density, and increase general well-being (Espinoza and Walston, *Cleveland Clinic Journal of Medicine*, 72 (12):1105-1112 (2005)).

Pharmaceutical treatments can include agents to improve appetite, analgesics, or hormone replacement therapy. Many of these traditional remedies are insufficient alone because they are limited to managing symptoms of the disease (such as pain), their efficacy is low, or they require the help or service of a caregiver (for example exercise or physical therapy).

The compounds and pharmaceutical compositions thereof can be administered, for example, parenterally (e.g., intramuscular, intraperitoneal, intravenous (IV) or subcutaneous) injection or infusion enterally (e.g., orally), or topically. Topical administration can include application to the lungs, nasal, oral (sublingual, buccal), vaginal, or rectal mucosa. In some embodiments, the compositions are administered in combination with transdermal or mucosal transport elements. In some embodiments, the composition is administered for e.g., days, weeks, months or years. In some embodiments, the composition is administered indefinitely, (e.g., as a nutraceutical with no duration limit). In some embodiments, the composition is administered daily.

EXAMPLES

Example I: Receptor-Based Virtual Screening

Methods and Materials

Methods for detecting kynurenine levels in cell culture media following IDO1 inhibitor treatment are as follows. The initial step in Phase I study was to develop an assay that could be utilized to measure kynurenine levels in vitro as a strategy to identify effective IDO1 inhibitors. Primary human myoblast cells (Gibco A12555) were treated with interferon gamma (100 ng/ml human IFN-gamma; R&D Systems cat. 285-IF) to increase IDO1 activity and then the cells were treated with various molecules previously been reported to suppress IDO1 activity. These inhibitors (10 µg/mL) included a known inhibitor of IDO1, indoximod (1-methyl-D-tryptophan), as well as a number of other compounds previously published as inhibiting IDO1, such as brassinin and rosmarinic acid. Kynurenine levels were measured in conditioned media 24 hrs after treatment and normalized to protein concentration of lysate in each well. Kynurenine levels were examined using ELISA performed at the Georgia Cancer Center and using LC/MS performed at the Medical College of Georgia (MCG) Proteomics Core Facility. Detection of kynurenine in samples was also performed using competitive ELISA kit (IBL America Cat #IB89190) according to manufacturer's instructions. In brief, 10 ul of samples and standards were mixed with 250 ul of acylation buffer and 25ul of acylation reagent and incubated for 90 min at 37° C. 20 ul of acylation reagent was used for 0/N incubation with Kynurenine Antiserum in Kynurenine Microtiter Strips. The next day, wells were washed and incubated for 30 min with 100 ul of goat anti-rabbit conjugated with perodixase. After washing, wells were incubated for 25 min with 100 ul of substrate followed by 100 ul stop solution. Absorbance at 450 nm was read using microplate reader. Standard curves and kynurenine concentration were calculated using R package installed on R 3.5.2. Limit of detection was calculated as the average of background samples minus 3×SD. Assay and data calculations were performed at Immune Monitoring Shared Resource (Augusta University). The data indicate that the two approaches (i.e. ELISA and LC/MS) yield similar results and are significantly correlated (P<0.01, r=0.94). ELISA assay was used for subsequent analyses as it was most effective for processing large numbers of samples.

Several molecules were screened to identify compounds that block IDO1 in primary human skeletal muscles cells and in vascular smooth muscle cells. Cells were treated with inhibitors as described above and kynurenine levels were analyzed using ELISA assay.

Results

Kynurenine levels were examined using ELISA performed at the Georgia Cancer Center and using LC/MS performed at the Medical College of Georgia (MCG) Proteomics Core Facility to determine the most effective outcome measure for identifying IDO1 activity and inhibition. As shown in FIGS. 1A and 1B, the results demonstrate that the two approaches yield similar results and are significantly correlated (P<0.01, r=0.94). The two bars in FIG. 1A represent replicates whereas the bars in FIG. 1B represent data from the LC/MS approach. Regardless which method was used, the outcomes were similar. ELISA assay was used for subsequent analyses as it was most effective for processing large numbers of samples.

Figures 2A, 2B:
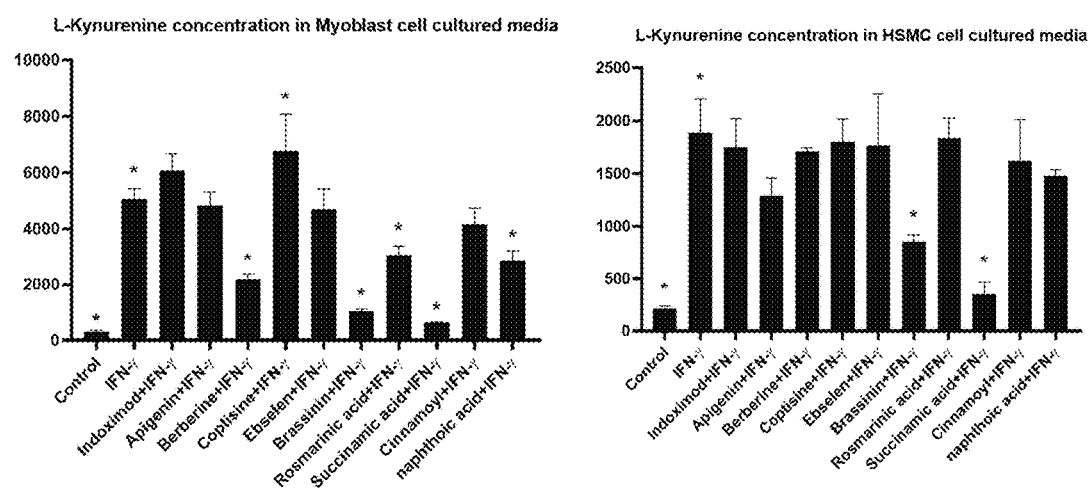
FIG. 2A shows L-kynurenine concentration in myoblast cell culture media and FIG. 2B shows L-kynurenine concentration in HSMC cell culture media. Cells were treated with inhibitors and kynurenine levels analyzed using ELISA.
Figure 3A:
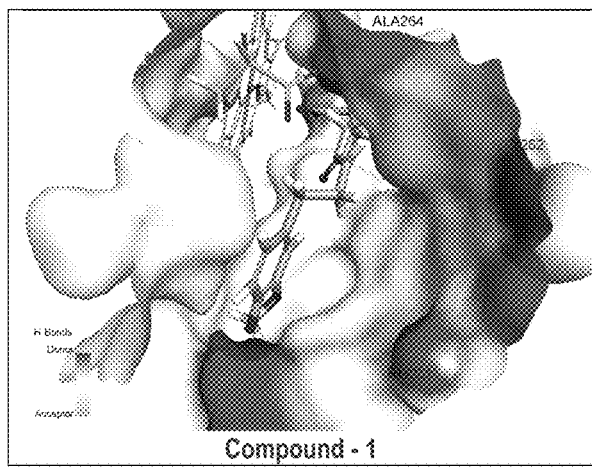
FIG. 3A-3D shows 3D depiction of compound 1 (FIG. 3A), compound 2 (FIG. 3B), compound 3 (FIG. 3C), and compound SA (FIG. 3D), respectively.
Figure 3B:
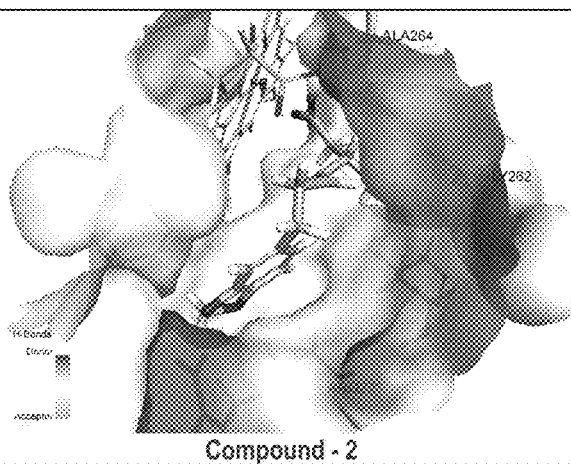
Figure 3C:
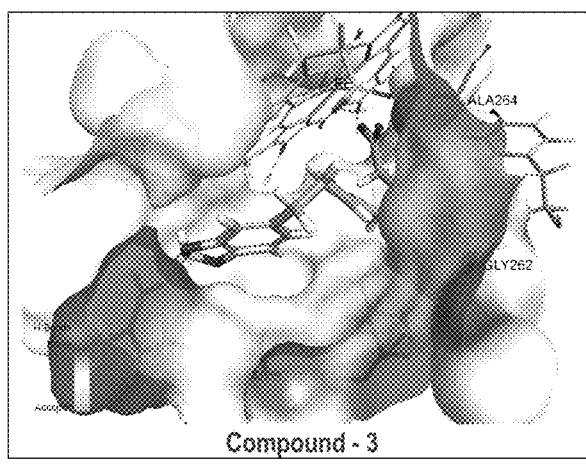
Figure 3D:
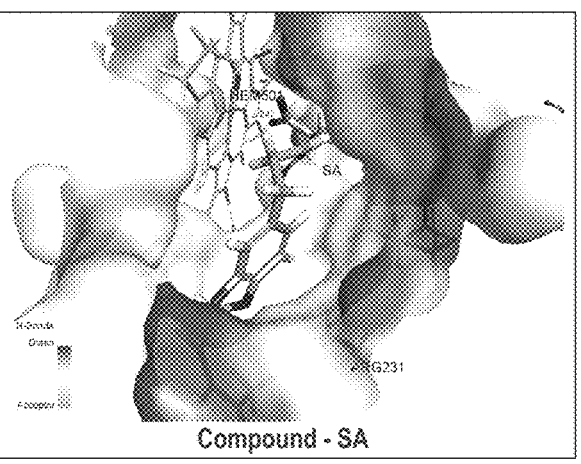

A known inhibitor of IDO1, Indoximod (1-methyl-D-tryptophan), as well as a number of other naturally occurring compounds previously published as inhibiting IDO1 (e.g., ebselin, brassinin, etc) were screened along with rosmarinic acid and its succinamic acid analog. Primary human skeletal muscle cells (FIG. 2A) or vascular smooth muscle cells (FIG. 2B) (Gibco) were treated with 100 ng/ml human IFN-gamma (R&D Systems cat. 285-IF) to increase IDO1 activity in the presence of the various inhibitors (10 µg/mL). Kynurenine levels were measured in conditioned media 24 hrs after treatment and normalized to protein concentration of lysate in each well. As shown in FIGS. 1A and 1B, the results demonstrate that Indoximod is a weak inhibitor of IDO1 in muscle cells, whereas several compounds, such as brassinin and the succinamic acid analog, significantly reduced KYN levels by more than 50% compared to cells exposed to IFN gamma alone.

Example II: Chemical Synthesis

Compounds described herein, salts and prodrugs thereof can be synthesized by conjugating equimolar quantities of a corresponding carboxylic acid and amine using isobutyl chloroformate as an activating agent for carboxylic acid. Reaction mixture was then taken to dryness and the product was isolated via column chromatography.

The structures of exemplary compounds 1, 2, 3, and 7 are shown below.

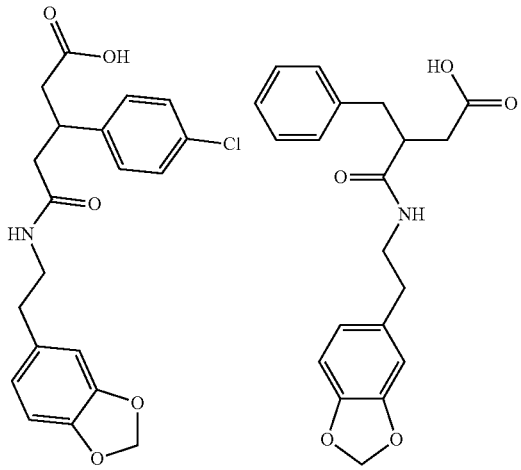

-continued

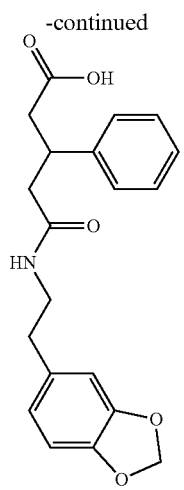

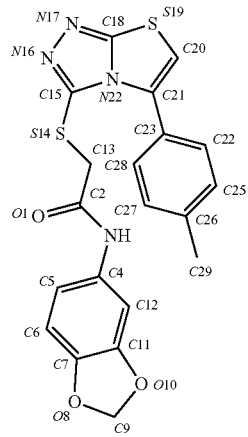

N-(1,3-benzodioxol-5-yl)-2-{[5-(4-methylphenyl)[1,3]thiazolo[2,3-c][1,2,4]triazol-3-yl]sulfanyl}acetamide PJK (From PDB)

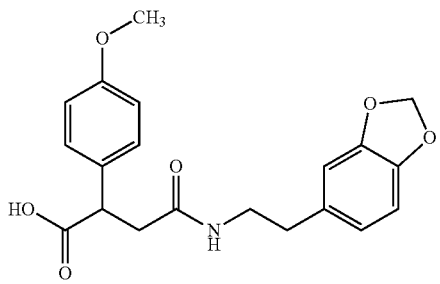

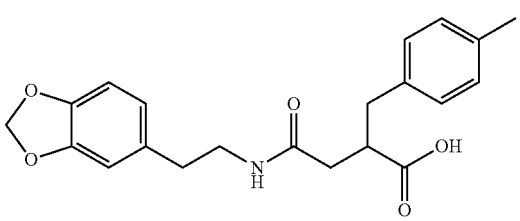

N-(2-Benzo[1,3]dioxol-5-yl-ethyl)-2-(4-methyl-benzyl)-succinamic acid

SA

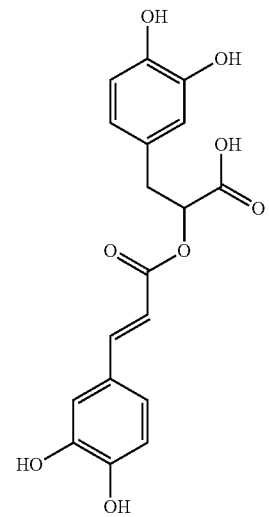

(2R)-3-(3,4-dihydroxyphenyl)-2-[(E)-3-(3,4-dihydroxyphenyl)pro-2-enoyl]oxypropanoic acid RA-Rosmarinic acid Example III: Molecular Docking Studies Methods and Materials Molecular docking analysis was carried out on the pocket sites as discussed by Meng, et al., *Curr. Comput. Aided Drug Des.*, 7 (2):146-157 (2011). Docking was carried out to allow a hybrid approach to calculate the free binding energies and binding affinity using MMGBSA approach. Inter- and Intra-ligand clashes were analyzed and torsions were analyzed to check the possibility of presence of dihedrals in CSD dataset for validation purpose. 2D depiction of the interactions were generated using PoseView.

Results

Molecular Docking Data

The crystal structures of indoleamine 2,3-dioxygenagse 1 (IDO1) complexed with Amg-1 Reference Ligands: SA, RA and PJK, respectively, and with exemplary compounds disclosed herein, respectively, were obtained (FIGS. 3A-3D).

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

5. The compound of claim 1 having the structure
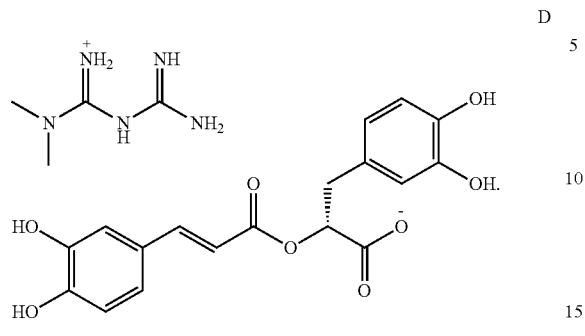

We claim:

1. A compound having the structure of

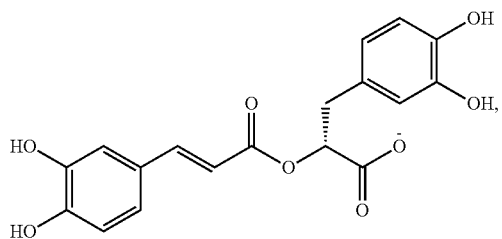
A

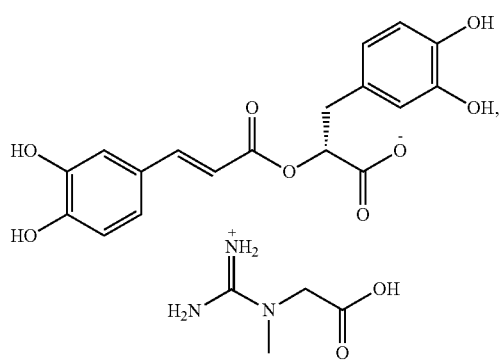
B

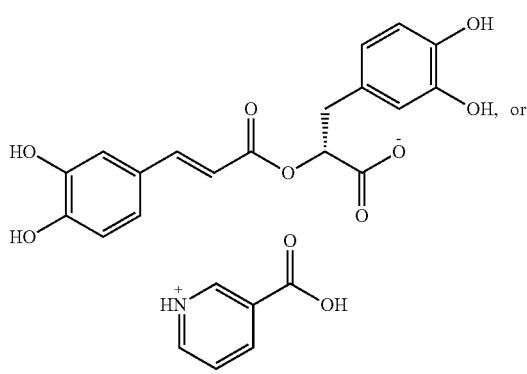
C, or

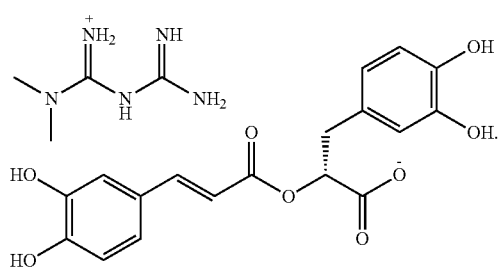
D

2. The compound of claim 1 having the structure

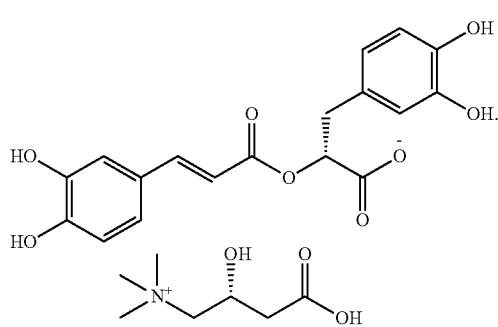
A

3. The compound of claim 1 having the structure

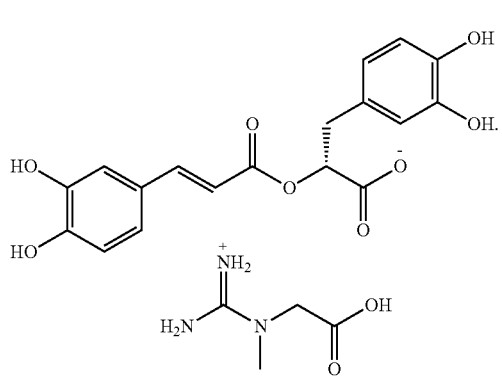
B

4. The compound of claim 1 having the structure

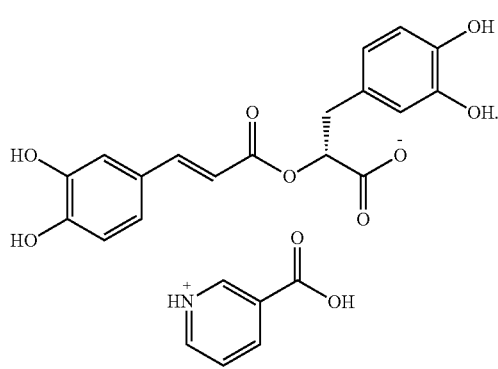
C